(12) United States Patent
Young et al.

(10) Patent No.: US 9,993,328 B2
(45) Date of Patent: Jun. 12, 2018

(54) ADVANCED KINK RESISTANT STENT GRAFT

(71) Applicant: TriVascular, Inc., Santa Rosa, CA (US)

(72) Inventors: Sarah Young, Menlo Park, CA (US); Cheng Li, Redwood City, CA (US); Michael V. Chobotov, Santa Rosa, CA (US); Patrick Stephens, Santa Rosa, CA (US); Robert G. Whirley, Santa Rosa, CA (US)

(73) Assignee: TriVascular, Inc., Santa Rosa, CA (US)

( * ) Notice: Subject to any disclaimer, the term of this patent is extended or adjusted under 35 U.S.C. 154(b) by 741 days.

(21) Appl. No.: 13/803,046

(22) Filed: Mar. 14, 2013

(65) Prior Publication Data

US 2013/0261734 A1 Oct. 3, 2013

Related U.S. Application Data

(60) Provisional application No. 61/619,715, filed on Apr. 3, 2012.

(51) Int. Cl.
*A61F 2/07* (2013.01)
*A61F 2/06* (2013.01)
(Continued)

(52) U.S. Cl.
CPC .............. *A61F 2/06* (2013.01); *A61F 2/07* (2013.01); *A61L 31/048* (2013.01); *A61L 31/146* (2013.01); *A61F 2/88* (2013.01); *A61F 2/89* (2013.01); *A61F 2002/065* (2013.01); *A61F 2002/067* (2013.01); *A61F 2002/072* (2013.01); *A61F 2002/825* (2013.01); *A61F 2002/91516* (2013.01); *A61F 2002/91541* (2013.01); *A61F 2230/0078* (2013.01); *A61F 2250/0003* (2013.01); *Y10T 29/49927* (2015.01)

(58) Field of Classification Search
CPC .......... A61F 2002/072; A61F 2002/077; A61F 2/885
See application file for complete search history.

(56) References Cited

U.S. PATENT DOCUMENTS 5,843,162 A     12/1998   Inoue
5,855,598 A *   1/1999   Pinchuk .................... A61F 2/07
                                                       623/1.13
(Continued)

FOREIGN PATENT DOCUMENTS

JP            3107397 B2     9/2000
JP       2007-537779 A    12/2007
(Continued)

OTHER PUBLICATIONS

PCT Partial Search Report dated Jul. 23, 2013.
Japanese Office Action for a counterpart foreign application dated Feb. 1, 2017.

*Primary Examiner* — Brian Pellegrino

(57) ABSTRACT

Stent-grafts for treating thoracic aortic aneurysms and abdominal aortic aneurysms include graft portions having inflatable channels and graft extensions. The graft extensions include an undulating wire stent and porous, but substantially fluid impermeable, polytetrafluoroethylene (PTFE) graft materials.

9 Claims, 13 Drawing Sheets

(51) Int. Cl.
*A61L 31/04* (2006.01)
*A61L 31/14* (2006.01)
*A61F 2/88* (2006.01)
*A61F 2/89* (2013.01)
*A61F 2/82* (2013.01)
*A61F 2/915* (2013.01)

(56) References Cited

U.S. PATENT DOCUMENTS

| | | | |
|---|---|---|---|
| 5,938,697 A * | 8/1999 | Killion | A61F 2/915 623/1.15 |
| 6,551,350 B1 | 4/2003 | Thornton et al. | |
| 2003/0120331 A1 * | 6/2003 | Chobotov | A61F 2/07 623/1.13 |
| 2005/0240261 A1 | 10/2005 | Rakos et al. | |
| 2006/0222596 A1 | 10/2006 | Askari et al. | |
| 2007/0173917 A1 * | 7/2007 | Hayashi | A61F 2/07 623/1.1 |
| 2007/0208409 A1 | 9/2007 | Quigley | |
| 2009/0125095 A1 * | 5/2009 | Bui | A61F 2/07 623/1.13 |
| 2013/0085565 A1 * | 4/2013 | Eller | A61F 2/07 623/1.46 |

FOREIGN PATENT DOCUMENTS

| | | |
|---|---|---|
| JP | 2010-540190 A | 12/2010 |
| WO | 2005/086942 A2 | 9/2005 |
| WO | 2007100456 A1 | 9/2007 |
| WO | 2009/046372 A2 | 4/2009 |
| WO | 2009046372 A2 | 4/2009 |

\* cited by examiner

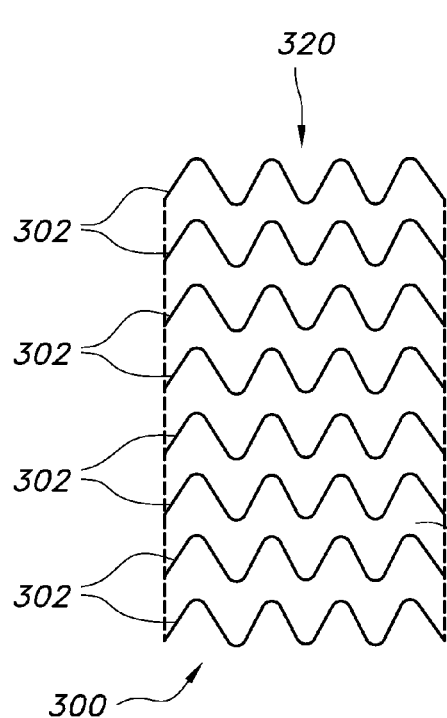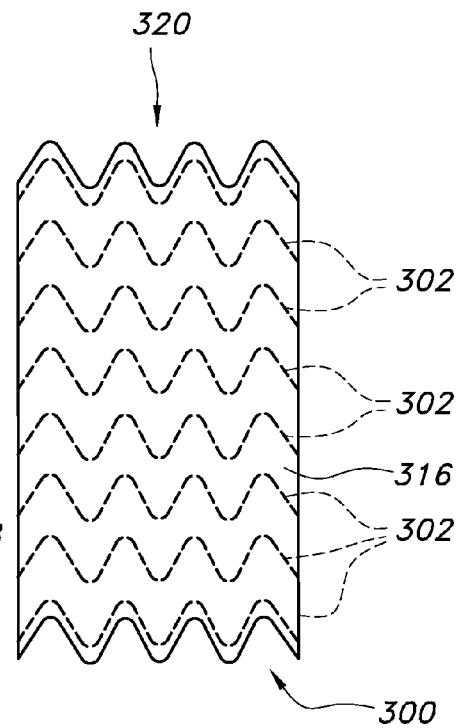
FIG. 11A  FIG. 11B
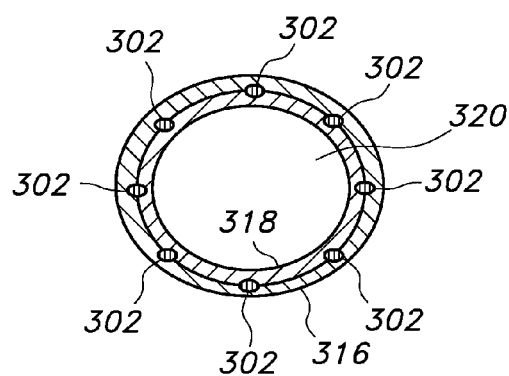
FIG. 12

ADVANCED KINK RESISTANT STENT GRAFT

CROSS-REFERENCE TO RELATED APPLICATIONS

This application claims the benefit of U.S. Provisional Application No. 61/619,715, filed Apr. 3, 2012, the contents of which are incorporated herein by reference.

FIELD OF THE INVENTION

The present invention relates to implantable devices for treating diseased bodily lumens. More particularly, the present invention relates to stent-grafts for treating thoracic aortic aneurysms and abdominal aortic aneurysms.

BACKGROUND

An aneurysm is a medical condition indicated generally by an expansion and weakening of the wall of an artery of a patient. Aneurysms can develop at various sites within a patient's body. Thoracic aortic aneurysms (TAAs) or abdominal aortic aneurysms (AAAs) are manifested by an expansion and weakening of the aorta which is a serious and life threatening condition for which intervention is generally indicated. Existing methods of treating aneurysms include invasive surgical procedures with graft replacement of the affected vessel or body lumen or reinforcement of the vessel with a graft.

Surgical procedures to treat aortic aneurysms can have relatively high morbidity and mortality rates due to the risk factors inherent to surgical repair of this disease as well as long hospital stays and painful recoveries. This is especially true for surgical repair of TAAs, which is generally regarded as involving higher risk and more difficulty when compared to surgical repair of AAAs.

Due to the inherent risks and complexities of surgical repair of aortic aneurysms, endovascular repair has become a widely-used alternative therapy, most notably in treating AAAs. Commercially available endoprostheses for the endovascular treatment of AAAs include the AneuRx® stent graft manufactured by Medtronic, Inc. of Minneapolis, Minn., the Zenith® stent graft system sold by Cook, Inc. of Bloomington, Ind., the PowerLink® stent-graft system manufactured by Endologix, Inc. of Irvine, Calif., and the Excluder® stent graft system manufactured by W.L. Gore & Associates, Inc. of Newark, Del. A commercially available stent graft for the treatment of TAAs is the TAG™ system manufactured by W.L. Gore & Associates, Inc.

An endovascular prosthesis must withstand tremendous pulsatile forces over a substantial period of time while remaining both seated and sealed within the vessel. In order to achieve these objectives, the device, which may comprise component parts and/or materials, must remain intact. The device must resist axial migration from the site of deployment while being subjected to significant pulsatile forces, and it should have sufficient radial compliance to conform to the vessel anatomy within which it is deployed so as to prevent blood leakage between the device and the vessel wall at both its proximal, or cephalic, end as well as at its distal, or caudal, end or ends (where the net force may be retrograde). Such a device should conform to the morphology of the treated vessel, without kinking or twisting, over the life of the patient.

SUMMARY OF THE INVENTION

The present invention is directed to kink-resistant endovascular devices, in particular endovascular stent-grafts. The endovascular devices of the present invention are use, but not limited to, for treating, thoracic aortic aneurysms and abdominal aortic aneurysms.

Some embodiments of a modular endovascular graft assembly include a bifurcated main graft member formed from a supple graft material having a main fluid flow lumen therein. The main graft member may also include an ipsilateral leg with an ipsilateral fluid flow lumen in communication with the main fluid flow lumen, a contralateral leg with a contralateral fluid flow lumen in communication with the main fluid flow lumen and a network of inflatable channels disposed on the main graft member. The network of inflatable channels may be disposed anywhere on the main graft member including the ipsilateral and contralateral legs. In addition, several inflatable channels may include a separate longitudinal channel in communication therewith, to provide additional support and rigidity to the device. The network of inflatable channels may be configured to accept a hardenable fill or inflation material to provide structural rigidity to the main graft member when the network of inflatable channels is in an inflated state. The network of inflatable channels may also include at least one inflatable cuff disposed on a proximal portion of the main graft member which is configured to seal against an inside surface of a patient's vessel. The fill material can also have transient or chronic radiopacity to facilitate the placement of the modular limbs into the main graft member. A proximal anchor member may be disposed at a proximal end of the main graft member and be secured to the main graft member. The proximal anchor member may have a self-expanding proximal stent portion secured to a self-expanding distal stent portion with struts having a cross sectional area that is substantially the same as or greater than a cross sectional area of proximal stent portions or distal stent portions adjacent the strut. At least one ipsilateral graft extension having a fluid flow lumen disposed therein may be deployed with the fluid flow lumen of the graft extension sealed to and in fluid communication with the fluid flow lumen of the ipsilateral leg of the main graft member. At least one contralateral graft extension having a fluid flow lumen disposed therein may be deployed with the fluid flow lumen of the graft extension sealed to and in fluid communication with the fluid flow lumen of the contralateral leg of the main graft member. For some embodiments, an outside surface of the graft extension may be sealed to an inside surface of the contralateral leg of the main graft when the graft extension is in a deployed state. For some embodiments, the axial length of the ipsilateral and contralateral legs may be sufficient to provide adequate surface area contact with outer surfaces of graft extensions to provide sufficient friction to hold the graft extensions in place. For some embodiments, the ipsilateral and contralateral legs may have an axial length of at least about 2 cm. For some embodiments, the ipsilateral and contralateral legs may have an axial length of about 2 cm to about 6 cm, more specifically, about 3 cm to about 5 cm.

Some embodiments of a modular endovascular graft assembly include a bifurcated main graft member having an axial length of about 5 cm to about 10 cm formed from a supple graft material. The main graft member has a main fluid flow lumen therein, an ipsilateral leg with an ipsilateral fluid flow lumen in communication with the main fluid flow lumen and with an axial length of at least about 2 cm, a contralateral leg with a contralateral fluid flow lumen in communication with the main fluid flow lumen and with an axial length of at least about 2 cm. The main graft member also includes network of inflatable channels disposed on the main graft member, including the ipsilateral and contralateral legs, which is configured to accept a hardenable fill material to provide structural rigidity to the main graft member when the network of inflatable channels are in an inflated state. Some or all of the inflatable channels may include a longitudinal inflatable channel in communication therewith so as to provide additional support and rigidity to the device. The network of inflatable channels may also include at least one inflatable cuff disposed on a proximal portion of the main graft member configured to seal against an inside surface of a patient's vessel. A proximal anchor member may be disposed at a proximal end of the main graft member and secured to the main graft member. The proximal anchor member may have a self-expanding proximal stent portion secured to a self-expanding distal stent portion with struts. At least one ipsilateral graft extension having a fluid flow lumen disposed therein may have the fluid flow lumen of the graft extension sealed to and in fluid communication with the fluid flow lumen of the ipsilateral leg of the main graft member. At least one contralateral graft extension having a fluid flow lumen disposed therein may have the fluid flow lumen of the graft extension sealed to and in fluid communication with the fluid flow lumen of the contralateral leg of the main graft member.

Some embodiments of a method of treating a patient include providing a delivery catheter containing a radially constrained bifurcated main graft member. The main graft member may be formed from a supple graft material which has a main fluid flow lumen therein and which has an ipsilateral leg with an ipsilateral fluid flow lumen in communication with the main fluid flow lumen and a contralateral leg with a contralateral fluid flow lumen in communication with the main fluid flow lumen. The main graft member may also include a network of inflatable channels disposed on the main graft member. Inflatable channels of the network of inflatable channels may be disposed on any portion of the main graft member including the ipsilateral and contralateral legs of the main graft member. The main graft member may also include a proximal anchor member which is disposed at a proximal end of the main graft member and secured to the main graft member. The proximal anchor member may have a self-expanding proximal stent portion secured to a self-expanding distal stent portion. Such a delivery catheter may be axially positioned within the patient's vasculature such that the main graft member within the delivery catheter is disposed coextensively with a vascular defect of the patient's aorta. Once this positioning has been achieved, the proximal anchor member may be deployed so as to radially expand and engage an inner surface of the patient's vasculature and anchor the proximal anchor member to the patient's aorta. Thereafter, the network of inflatable channels of the main graft member may be inflated with an inflation material so as to provide a more mechanically rigid structure of the main graft member. For some embodiments, inflation of the network of inflatable channels may also provide a seal between an outer surface of an inflatable cuff of the main graft member and an inside surface of the patient's body lumen in contact with the inflatable cuff. For some embodiments, a hardenable fill material may be used that may assume or more solid configuration after inflation of the network of inflatable channels so as to provide additional mechanical rigidity as well as prevent leakage of the fill material. Some embodiments may also employ radiopaque inflation material to facilitate monitoring of the fill process and subsequent engagement of graft extensions. A second delivery catheter containing a radially constrained self-expanding contralateral graft extension may then be axially positioned in the contralateral leg of the main graft member with a proximal portion of the contralateral graft extension axially overlapped with an inner fluid flow lumen of the contralateral leg of the main graft member and a distal portion of the contralateral graft extension axially overlapped with a portion of the patient's contralateral iliac artery. Access to the contralateral leg of the main graft portion may be achieved by percutaneous access or femoral arteriotomy from the patient's contralateral femoral artery with a delivery sheath or the like. Once properly positioned, the self-expanding contralateral graft extension may be deployed by releasing the radial constraint of the second delivery catheter. As the contralateral graft extension self-expands in an outward radial orientation, a seal between the inner fluid flow lumen of the contralateral graft extension, a fluid flow lumen of the contralateral leg and a fluid flow lumen of the contralateral iliac artery may be formed. A third delivery catheter containing a radially constrained self-expanding ipsilateral graft extension may also be axially positioned in the ipsilateral leg of the main graft member with a proximal portion of the ipsilateral graft extension axially overlapped with an inner fluid flow lumen of the ipsilateral leg of the main graft member and a distal portion of the ipsilateral graft extension axially overlapped with a portion of the patient's ipsilateral iliac artery. The self-expanding ipsilateral graft extension may then be deployed by releasing the radial constraint so as to form a seal between the inner fluid flow lumen of the ipsilateral graft extension, a fluid flow lumen of the ipsilateral leg and a fluid flow lumen of the ipsilateral iliac artery. The ipsilateral and contralateral graft extensions may be delivered and deployed in either order.

Some embodiments of a graft extension include a fluid flow lumen disposed therein, at least one layer of permeable PTFE material, at least one layer of semi-permeable or substantially non-permeable PTFE material having no discernable node and fibril structure and an interposed self-expanding stent formed from an elongate resilient element helically wound with a plurality of longitudinally spaced turns into an open tubular configuration disposed between at least one outer layer and at least one inner layer of PTFE material.

In some embodiments, there is provided an endovascular stent-graft including: a tubular stent wall having opposed first and second ends; an undulating wire having opposed first and second ends and being helically wound into a plurality of approximate circumferential windings to define the stent wall; the undulating wire having a plurality of undulations defined by peaks and valleys; peaks of adjacent approximate circumferential windings being separated by a distance with the distance between peaks at the first end being different from the distance between peaks at the second end; the first wire end secured to a first undulation at the first end; the second wire end secured to a second undulation at the second end; a graft liner including first plurality of layers of porous PTFE having no discernable node and fibril structure; a graft covering including a second plurality of layers of porous PTFE having no discernable node and fibril structure; and where the tubular stent wall is securably disposed between the graft covering and the graft lining.

Other embodiments include an endovascular stent-graft including: a graft liner including first plurality of layers of porous PTFE having no discernable node and fibril structure; a graft covering including a second plurality of layers of porous PTFE having no discernable node and fibril structure; and a tubular stent securably disposed between the graft liner and the graft cover; the stent including an undulating wire having opposed first and second ends and being helically wound into a plurality of approximate circumferential windings to define a stent wall; the undulating wire having a plurality undulations defined by peaks and valleys with peaks of adjacent approximate circumferential windings being separated by a distance; where the graft liner and the graft covering is crimped between the peaks of adjacent approximate circumferential windings to provide crimped graft portions.

There may be provided a method of making a crimped stent graft, including the steps of: providing a tubular stent having an inner surface and an outer surface, the stent including an undulating wire having opposed first and second ends and being helically wound into a plurality of approximate circumferential windings to define a stent wall; the undulating wire having a plurality undulations defined by peaks and valleys with peaks of adjacent approximate circumferential windings being separated by a distance; axially stretching the tubular stent; disposing a graft liner on the inner surface of the axially stretched tubular stent, the graft liner including first plurality of layers of porous PTFE having no discernable node and fibril structure; disposing a graft covering on the outer surface of the axially stretched tubular stent, the graft covering including a second plurality of layers of porous PTFE having no discernable node and fibril structure; and allowing the axially stretched tubular stent to relax, forming crimps in the graft liner and the graft covering.

Other embodiments include a method of making a crimped stent graft, including the steps of: providing a tubular stent having an inner surface and an outer surface, the stent including an undulating wire having opposed first and second ends and being helically wound into a plurality of approximate circumferential windings to define a stent wall; the undulating wire having a plurality undulations defined by peaks and valleys with peaks of adjacent approximate circumferential windings being separated by a distance; disposing a graft liner on the inner surface of the axially stretched tubular stent, the graft liner including first plurality of layers of porous PTFE having no discernable node and fibril structure; disposing a graft covering on the outer surface of the axially stretched tubular stent, the graft covering including a second plurality of layers of porous PTFE having no discernable node and fibril structure; placing the tubular stent, graft liner and graft cover on a shaped mandrel, the shaped mandrel including at least one crimp shape on its outer surface; and heating and sintering the tubular stent, graft liner and graft cover so as to form a crimped stent graft including at least one crimp conforming to the crimp shape of the shaped mandrel.

Still other embodiments of the present invention include an inflatable endovascular graft including a tubular graft having opposed first and second open ends and having a first graft portion proximal to the first end and a second graft portion proximal to the second end; at least one circumferential inflatable channel disposed at the first graft portion; at least two circumferential inflatable channels disposed at the second graft portion; a longitudinal inflatable fill channel disposed between the first end and the second end of the graft and in fluid communication with the at least one circumferential inflatable channel disposed at the first graft portion and the at least two circumferential inflatable channels disposed at the second graft portion; a first longitudinal inflatable channel disposed along the second graft portion and traversing the at least two circumferential inflatable channels disposed at the second graft portion, where the first longitudinal inflatable channel is in fluid communication with the at least two circumferential inflatable channels disposed at the second graft portion.

The present invention may further include a bifurcated inflatable endovascular graft including a tubular graft having a first end and a second opposed bifurcated end, the second bifurcated end having a first branch and a second branch, the first end having a first graft portion proximal to the first end, the first branch having a first branch portion proximal to the second end, the second branch having a second branch portion proximal to the second end; at least one circumferential inflatable channel disposed at the first graft portion; at least two circumferential inflatable channels disposed at the first branch portion; at least two circumferential inflatable channels disposed at the second branch portion; a first longitudinal inflatable fill channel disposed between the first end and the end of the first branch portion and in fluid communication with the at least one circumferential inflatable channel disposed at the first graft portion and the at least two circumferential inflatable channels disposed at the first branch portion; a second longitudinal inflatable fill channel disposed between the first end and the end of the second branch portion and in fluid communication with the at least one circumferential inflatable channel disposed at the first graft portion and the at least two circumferential inflatable channels disposed at the second branch portion; a first longitudinal inflatable channel dispose along the first branch portion and traversing the at least two circumferential inflatable channels disposed at the first branch portion, where the first longitudinal inflatable channel is in fluid communication with the at least two circumferential inflatable channels disposed at the first branch portion; and a second longitudinal inflatable channel dispose along the second branch portion and traversing the at least two circumferential inflatable channels disposed at the second branch portion, where the second longitudinal inflatable channel is in fluid communication with the at least two circumferential inflatable channels disposed at the second branch portion.

Other embodiments include a modular endovascular graft including a tubular graft having a first end and a second opposed bifurcated end, the second bifurcated end having a first branch and a second branch, the first end having a first graft portion proximal to the first end, the first branch having a first branch portion proximal to the second end, the second branch having a second branch portion proximal to the second end; at least one circumferential inflatable channel disposed at the first graft portion; at least two circumferential inflatable channels disposed at the first branch portion; at least two circumferential inflatable channels disposed at the second branch portion; a first longitudinal inflatable fill channel disposed between the first end and the end of the first branch portion and in fluid communication with the at least one circumferential inflatable channel disposed at the first graft portion and the at least two circumferential inflatable channels disposed at the first branch portion; a second longitudinal inflatable fill channel disposed between the first end and the end of the second branch portion and in fluid communication with the at least one circumferential inflatable channel disposed at the first graft portion and the at least two circumferential inflatable channels disposed at the second branch portion; a first longitudinal inflatable channel dispose along the first branch portion and traversing the at least two circumferential inflatable channels disposed at the first branch portion, where the first longitudinal inflatable channel is in fluid communication with the at least two circumferential inflatable channels disposed at the first branch portion; a second longitudinal inflatable channel dispose along the second branch portion and traversing the at least two circumferential inflatable channels disposed at the second branch portion, where the second longitudinal inflatable channel is in fluid communication with the at least two circumferential inflatable channels disposed at the second branch portion; a first stent-graft securable to the first branch portion; and a second stent-graft securable to the second branch portion.

The modular graft may include a first and/or second stent-graft including a tubular stent wall having opposed first and second ends; an undulating wire having opposed first and second ends and being helically wound into a plurality of approximate circumferential windings to define the stent wall; the undulating wire having a plurality undulations defined by peaks and valleys; peaks of adjacent approximate circumferential windings being separated by a distance with the distance between peaks at the first end being different from the distance between peaks at the second end; the first wire end secured to a first undulation at the first end; the second wire end secured to a second undulation at the second end; a graft liner including first plurality of layers of porous PTFE having no discernable node and fibril structure; a graft covering including a second plurality of layers of porous PTFE having no discernable node and fibril structure; and where the tubular stent wall is securably disposed between the graft covering and the graft lining.

These features of embodiments will become more apparent from the following detailed description when taken in conjunction with the accompanying exemplary drawings.

BRIEF DESCRIPTION OF THE DRAWINGS

FIGS. 11A and 11B depict stent graft assemblies useful in the present invention.

FIG. 12 is a top cross sectional view of one embodiment of a stent graft assembly of the present invention.

DETAILED DESCRIPTION OF THE INVENTION

Figure 1:
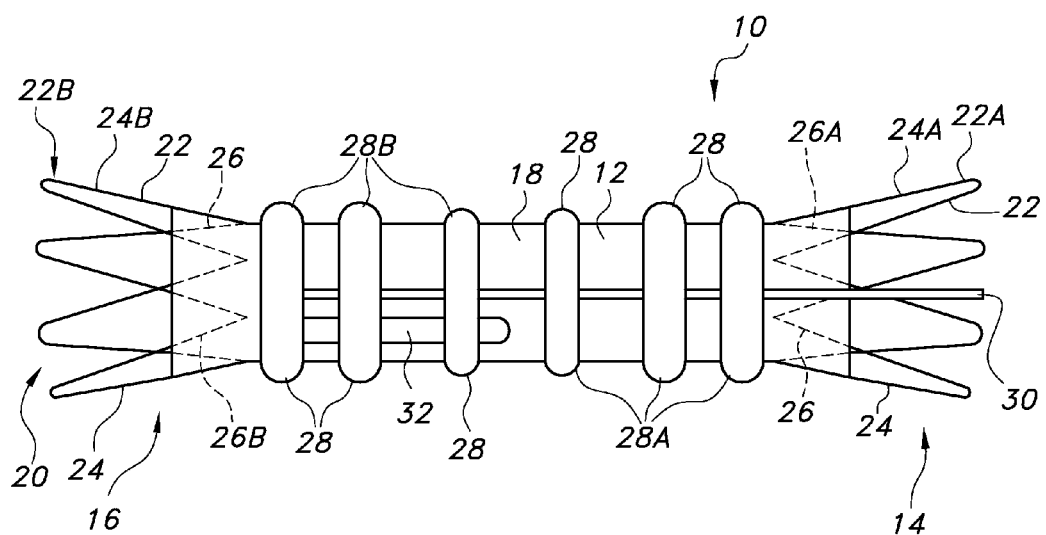
FIG. 1 is an elevation view of a graft assembly useful for treating, but not limited to, thoracic aortic aneurysms according to the present invention.

Embodiments of the invention are directed generally to methods and devices for treatment of fluid flow vessels with the body of a patient. Treatment of blood vessels is specifically indicated for some embodiments, and, more specifically, treatment of aneurysms, such as, but not limited to, thoracic aortic aneurysms and abdominal aortic aneurysms. The present invention provides various graft assemblies for treatment of blood vessels, including modular graft assemblies, bifurcated graft assemblies, stent-graft assemblies, and combinations thereof.

Modular graft assemblies of the present invention may include a main graft assembly having a network of inflatable channels and a graft. One end the graft assembly may include a graft extension, disposed at, for example, a distal end of the assembly. The graft assembly may be bi-furcated or non-bifurcated. The graft assembly may be formed from a supple graft material, such as ePTFE, having a main fluid flow lumen therein. The graft assembly may include porous PTFE which has no discernable node and fibril structure. The bifurcated graft assembly may also include an ipsilateral leg with an ipsilateral fluid flow lumen in communication with the main fluid flow lumen, a contralateral leg with a contralateral fluid flow lumen in communication with the main fluid flow lumen, and a network of inflatable channels disposed on the main graft member. For some embodiments, the main graft member may have an axial length of about 5 cm to about 10 cm, more specifically, about 6 cm to about 8 cm in order to span an aneurysm of a patient's aorta without engaging the patient's iliac arteries directly with the legs of the main graft member.

The inflatable channels of the network of inflatable channels may be disposed on any portion of the graft assembly including the main body portion, as well as the ipsilateral and contralateral legs. The network of inflatable channels may be configured to accept a hardenable fill material to provide structural rigidity to the main graft member when the network of inflatable channels are in an inflated state and the inflation material has been cured or hardened. Radiopaque inflation material may be used to facilitate monitoring of the fill process and subsequent engagement of graft extensions. The network of inflatable channels may also include at least one inflatable cuff disposed on a proximal portion of the main graft member which is configured to seal against an inside surface of a patient's vessel, such as the aorta. The network of inflatable channels may include at least one longitudinal fill channel in communication with channels at the proximal and distal ends of the device. Further, the network of inflatable channels may include a longitudinal channel in communication with circumferential channels at one end of the device.

A proximal anchor member may be disposed at a proximal end of the main graft member and secured to the main graft member. The proximal anchor member has a self-expanding proximal stent portion secured to a self-expanding distal stent portion with struts. Some embodiments of the struts may have a cross sectional area that is substantially the same as or greater than a cross sectional area of proximal stent portions or distal stent portions adjacent the strut. Such a configuration may be useful in avoiding points of concentrated stress in the proximal anchor member or struts which couple components thereof. For some embodiments, the proximal stent of the proximal anchor member further includes a plurality of barbs having sharp tissue engaging tips that are configured to extend in a radial outward direction in a deployed expanded state. For some embodiments, the proximal anchor member includes a 4 crown proximal stent portion and an 8 crown distal stent portion which may be made from a superelastic alloy such as superelastic nitinol (NiTi) alloy.

For a non-bifurcated graft assembly, at least one graft extension having a fluid flow lumen disposed therein may be deployed with the fluid flow lumen of the graft extension sealed to and in fluid communication with the fluid flow lumen of the main graft member. The graft extension may be disposed at the distal end of the main graft member. For a bifurcated graft assembly, at least one ipsilateral graft extension having a fluid flow lumen disposed therein may be deployed with the fluid flow lumen of the graft extension sealed to and in fluid communication with the fluid flow lumen of the ipsilateral leg of the main graft member. In addition, at least one contralateral graft extension having a fluid flow lumen disposed therein may be deployed with the fluid flow lumen of the graft extension sealed to and in fluid communication with the fluid flow lumen of the contralateral leg of the main graft member. For some embodiments, the graft extensions may include an interposed self-expanding stent disposed between at least one outer layer and at least one inner layer of supple layers of graft material. The interposed stent disposed between the outer layer and inner layer of graft material may be formed from an elongate resilient element helically wound with a plurality of longitudinally spaced turns into an open tubular configuration. In some embodiments, the interposed stent may have a winding, undulating configuration from the proximal end to the distal end. For some embodiments, the interposed stent is may include a superelastic alloy such as superelastic NiTi alloy. In addition, the graft material of each graft extension may further include at least one axial zone of low permeability for some embodiments.

For some embodiments, an outside surface of the graft extension may be sealed to an inside surface of the main graft or a leg of the main graft when the graft extension is in a deployed state. For some embodiments, the axial length of the ipsilateral and contralateral legs may be sufficient to provide adequate surface area contact with outer surfaces of graft extensions to provide sufficient friction to hold the graft extensions in place. For some embodiments, the ipsilateral and contralateral legs may have an axial length of at least about 2 cm. For some embodiments, the ipsilateral and contralateral legs may have an axial length of about 2 cm to about 6 cm, more specifically, about 3 cm to about 5 cm.

Figure 2A:
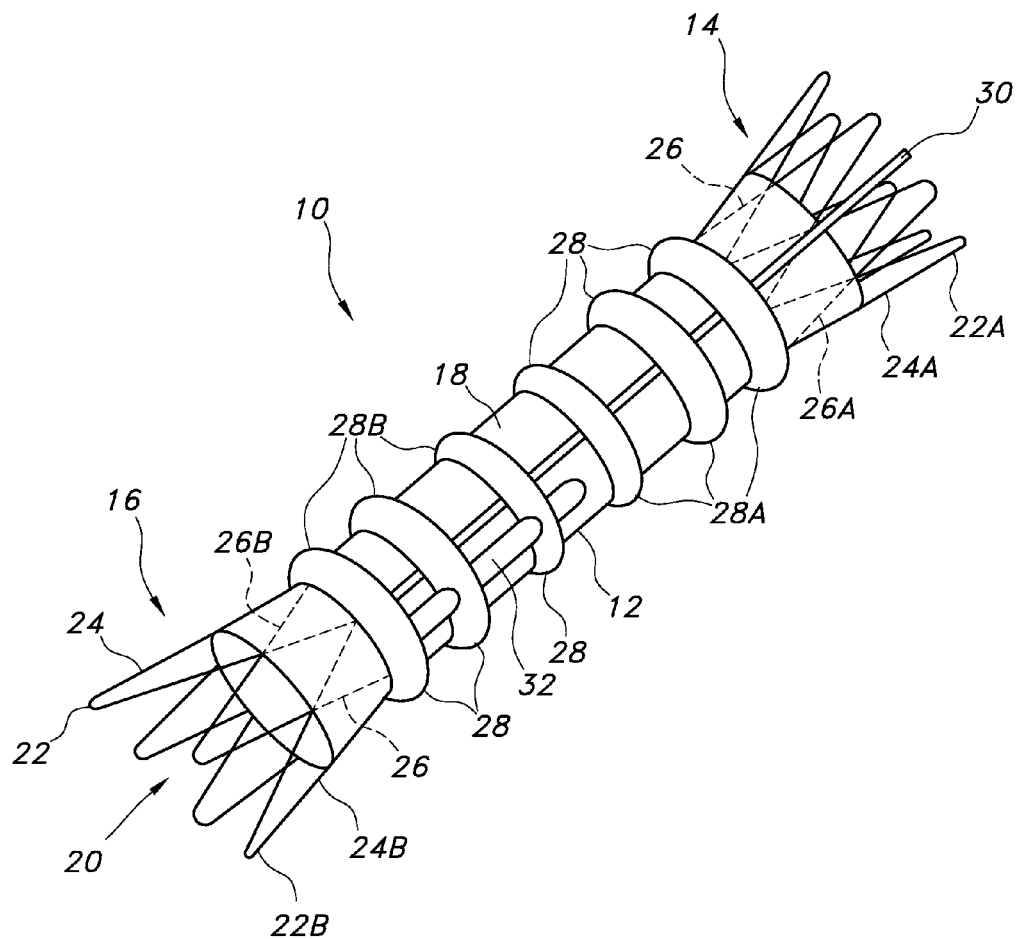
FIG. 2A is a perspective view of the graft assembly of FIG. 1.

FIGS. 1 and 2A depict a graft assembly 10 for the treatment of an aneurysm, such as, but not limited to, a thoracic aortic aneurysm. FIGS. 1 and 2A depict a graft assembly 10 that is non-bifurcated, but it will be understood that the assembly may include a bifurcated portion. As depicted in FIGS. 1 and 2A, the graft assembly 10 includes a main graft member 12 disposed between a proximal open end 14 and an opposed open distal end 16. The main graft 12 has a wall portion 18 that bounds a main fluid flow lumen 20 disposed therein and between the opposed open ends 14, 16. The graft wall portion 18 may be made from any biocompatible, durable material, including, for example, PTFE, Dacron, and the like. Unless otherwise specifically stated, the term "PTFE" as used herein includes PTFE, porous PTFE and ePTFE, any of which may be impermeable, semi-permeable, or permeable. Furthermore, the graft assembly 10 and any portions thereof including the main body and extensions described herein may include all PTFE, all ePTFE, or a combination thereof. In one particular embodiment, the graft wall portion 18 includes a porous PTFE material having no discernable node and fibril structure. Methods of formation of such materials include those methods described in U.S. Patent Application Publication No. 2006/0233990, which is incorporated by reference in its entirety herein.

With regard to graft embodiments discussed herein, such as graft assembly 10, and components thereof, the term "proximal" refers to a location towards a patient's heart and the term "distal" refers to a location away from the patient's heart. With regard to delivery system catheters and components thereof discussed herein, the term "distal" refers to a location that is disposed away from an operator who is using the catheter and the term "proximal" refers to a location towards the operator.

Figure 2B:
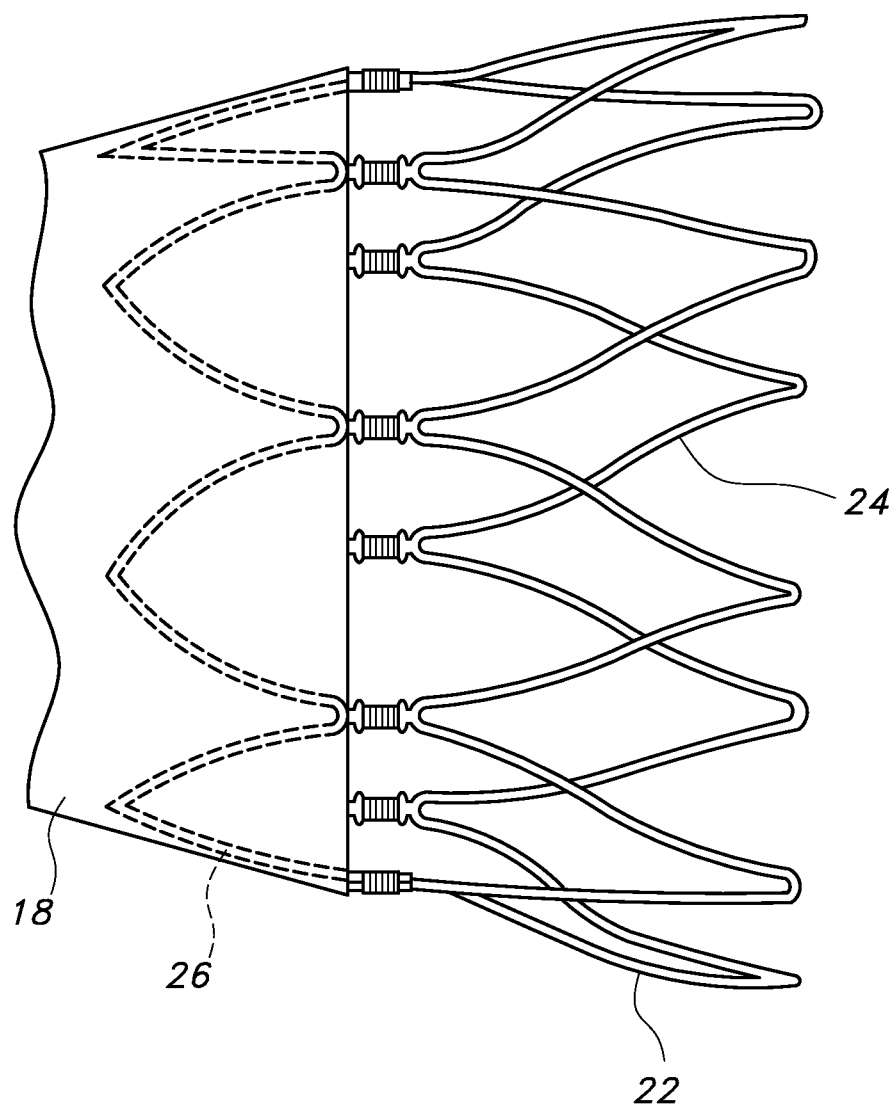
FIG. 2B depicts a close up view of a proximal anchor member and connector ring.

The graft assembly 10 may include a proximal anchor member 22A, which may be disposed at a proximal end 14 of the main graft 12. One representative anchor system may include one as depicted in FIG. 2B. The anchor member 22 includes a proximal stent 24, which may be self-expanding or may be balloon-expandable, that is formed from an elongate element having a generally serpentine shape with a number of crowns or apices at either end. As depicted in FIG. 2A, six crowns or apices are shown for stent 24A. The number of crowns or apices is not limiting and any suitable number may be used. As depicted in FIG. 2B, eight crowns or apices may be used. A distal and/or proximal end of the stent 24 may be mechanically coupled to a connector ring 26 which is embedded in graft material, either at the proximal end 14 of the main graft 12 or the distal end 16 of the main graft 12, or directly coupled to perforations in the proximal or distal edge region of the main graft. Embodiments of the connector ring 26 may be generally circular in shape have regular undulations about the circumference that may be substantially sinusoidal in shape. As depicted in FIGS. 1 and 2A, the proximal end 14 of the graft assembly 10 may include a proximal anchor member 22A. The proximal anchor member 22A may similarly include a proximal self-expanding stent 24A, which may be mechanically coupled to a proximal connector ring 26A. In addition, the assembly 10 may include a similar configuration at the distal end 16. The distal end 16 of the graft assembly 10 may include a distal anchor member 22B. The distal anchor member 22B may similarly include a distal self-expanding stent 24B, which may be mechanically coupled to a connector ring 26B. It is understood that the graft assembly 10 may include a proximal anchor member 22A only, a proximal anchor member 22A and a distal anchor member 22B, or neither of a proximal anchor member 22A or a distal anchor member 22B. U.S. Pat. No. 7,147,660, which is incorporated by reference herein, also includes anchor member embodiments that may be used for embodiments discussed herein.

Anchor member 22 may be configured as a self-expanding anchor member having an undulating pattern and may be made from stainless steel, nickel titanium alloy or any other suitable material. The anchor member 22 may be configured to be balloon expandable or self-expanding in an outward radial direction from a radially compressed state. The proximal anchor member 22 and its components may have the same or similar features, dimensions or materials to those of the stents described in U.S. Pat. No. 7,147,660, the content of which is hereby incorporated by reference in its entirety.

In a particularly desirable embodiment, a network of inflatable elements or channels (generally depicted as reference numeral 28) is disposed on the graft body 12. The graft assembly 10 may include at least one proximal circumferential inflatable channel 28A and at least one distal circumferential inflatable channel 28B. The inflatable channels 28 may extend around the entire circumference of the graft body 12 or may only extend partially around the circumference of the graft body 12. The at least one proximal circumferential inflatable channel 28A and the at least one distal circumferential inflatable channel 28B may be in communication with each other via a longitudinal inflatable fill channel 30. The longitudinal inflatable fill channel 30 is a tubular structure which is designed to allow communication between the interior of the inflatable channels 28A, 28B. The inflatable channels 28A, 28B may be inflated under pressure with an inflation material (not shown) through a longitudinal inflatable fill channel 30 that has a lumen disposed therein in fluid communication with the network of inflatable channels 28. The inflation material may be retained within the network of inflatable channels 28 by a one way-valve (not shown), disposed within the lumen of the longitudinal inflatable fill channel 30. The network of inflatable channels 28 may optionally be filled with a hardenable material that may be configured to harden, cure or otherwise increase in viscosity or become more rigid after being injected into the channels. Hardenable inflation materials such as gels, liquids or other flowable materials that are curable to a more solid or substantially hardened state may be used to provide mechanical support to the graft body 12 by virtue of the mechanical properties of the hardened material disposed within the channels 28. The network of inflatable channels 28 may also provide structural support to the graft body 12 when in an inflated state due to the stiffness of the channels created by the increased interior pressure within the channels even if a non-hardenable inflation material, such as saline or the like, is used so long as an increased interior pressure can be maintained. Such an increase in stiffness or rigidity may be useful for a variety of purposes. For example, during deployment, inflation of the network of inflatable channels 28 may urge the graft body 12 including the main flow channel and legs thereof to conform to a generally cylindrical configuration having open flow lumens which may be useful when attempting to locate and navigate the flow lumens of the graft assembly 10 with a delivery catheter, guidewire or the like. Such location and navigation of the flow lumens of the graft assembly 10 and portions thereof may also be facilitated by the use of radiopaque inflation materials that provide enhanced visualization under fluoroscopic imaging.

To provide further support and rigidity to the graft assembly 10, the graft assembly 10 may include a longitudinal inflatable channel 32, disposed between and in fluid communication with at least two circumferential inflatable channels 28. For example, the distal end 16 of the graft assembly 10 may include at least two distal circumferential inflatable channels 28B. This assembly is best seen in FIG. 2A. The longitudinal inflatable channel 32 is in communication with at least two distal circumferential channels 28B, and may be in fluid communication with more than two distal circumferential channels 28B. Such longitudinal inflatable channel 32 provides further support and rigidity to the assembly 10 when inflated. The longitudinal inflatable channel 32 may comprise a plurality of individual channels, each in communication with circumferential channels 28.

The network of inflatable channels 28 may include one or more circumferential channels disposed completely or partially about the graft body 12 as well as longitudinal or helical channels that may provide support as well as a conduit in communication with the circumferential channels 28 that may be used for filling the network of inflatable channels 28 with inflation material. Some embodiments may also employ radiopaque inflation material to facilitate monitoring of the fill process and subsequent engagement of graft extensions (when used). The network of inflatable channels 28 may also include one or more one or more enlarged circumferential channels in the form of inflatable cuffs. The inflatable cuff (or cuffs) are disposed towards the end of the graft body 12, such as at the proximal end 14 or distal end 16. One example of a proximal inflatable cuff is depicted in FIG. 2A as the circumferential inflatable channel 28A. An inflatable cuff or cuffs disposed at the ends of the body 12 may be configured to seal to an inside surface of a patient's vessel such as a patient's abdominal aorta. An inflatable cuff may be disposed on a portion of the main graft 12 distal of the proximal anchor member 22A and has an outer surface that extends radially from a nominal outer surface of the main graft 12. The inflatable cuff may be configured to expand radially beyond a nominal outer surface of the main graft 12 and provide a seal against an inside surface of a body lumen when the inflatable cuff is inflated with an inflation material to an expanded state. The axial separation of the proximal anchor member 22A and proximal inflatable cuff 28A allows for spatial separation of the primary anchoring mechanism and at least part of the sealing function which may allow the graft to be restrained or otherwise compressed to a smaller outer profile for deployment from a delivery catheter. An interior cavity of any inflatable channels 28 (including one or more inflatable cuffs) is in fluid communication with the interior cavity of the remaining network of inflatable channels 28 and may have a transverse dimension or inner diameter of about 0.040 inch to about 0.250 inch.

Some embodiments of main graft member 12 may include about 1 to about 8 circumferential inflatable channels disposed about the graft body 12. Some embodiments of the graft body 12 may include about 1 to about 4 longitudinal (or axial) inflatable fill channels 30 that may serve to connect the circumferential inflatable channels 28. Some embodiments of the circumferential channels 28 may extend a full circumference of the graft section upon which they are disposed, or they may extend only partially around the graft section upon which they are disposed. For the graft body embodiment 12 shown in FIGS. 1 and 2A, the network of inflatable channels 28 includes an inflatable cuff (28A) disposed adjacent the proximal end 14 of the main body portion of the graft body 12. A longitudinal or axial channel extends substantially along the graft body 12 in fluid communication with the circumferential channels 28 and proximal inflatable cuff 28A at the proximal end of the graft body 12. The longitudinal inflatable channel 32 extends between and is in fluid communication with three of the distal inflatable channels 28B. As the inflation material is disposed through the longitudinal fill channel 30, each of the inflatable channels 28 (including proximal inflatable cuff 28A and distal inflatable channels 28B) is filled with inflation material. In addition, the longitudinal inflatable channel 32 is filled with inflation material, resulting in a rigid and strong graft assembly 10.

Some of the inflatable channels 28 of the graft assembly 10 discussed herein may be disposed circumferentially and axially. Alternatively, such inflatable channels 28 may be disposed in spiral, helical, or other configurations. Examples of channel configurations suitable for embodiments of the present invention are described further in U.S. Pat. No. 7,150,758, the entirety of which is incorporated herein by reference. All inflatable channel embodiments described herein as circumferential, may alternatively take on any of the aforementioned alternative configurations. Other modular graft embodiments are discussed in U.S. Patent Application Publication No. 2006/0224232, by Chobotov et al. titled "Hybrid Modular Endovascular Graft", which is hereby incorporated by reference herein in its entirety.

The network of inflatable channels 28, including an inflatable cuff and longitudinal inflatable channel 32, may be filled during deployment of the graft with any suitable inflation material. As discussed above, the inflation material may be used to provide outward pressure or a rigid structure from within the network of inflatable channels 28. Biocompatible gases, liquids, gels or the like may be used, including curable polymeric materials or gels, such as the polymeric biomaterials described in U.S. Pat. No. 7,744,912 and entitled "Biomaterials Formed by Nucleophilic Addition Reaction to Conjugated Unsaturated Groups" to Hubbell et al.; U.S. Pat. No. 6,958,212 and entitled "Conjugate Addition Reactions for Controlled Delivery of Pharmaceutically Active Compounds" to Hubbell et al.; and further discussed in U.S. Pat. No. 7,147,660 and entitled "Advanced Endovascular Graft" to Chobotov, et al., each of which is incorporated by reference herein in its entirety. Some embodiments may use inflation materials formed from glycidyl ether and amine materials, as discussed in U.S. Patent Application Publication No. 2006/0222596 and entitled "Non-Degradable, Low-Swelling, Water Soluble Radiopaque Hydrogel Polymer" to Askari and Whirley, the contents of which are incorporated herein by reference. Some inflation material embodiments may include an in situ formed hydrogel polymer having a first amount of diamine and a second amount of polyglycidyl ether wherein each of the amounts are present in a mammal or in a medical device, such as an inflatable graft, located in a mammal in an amount to produce an in situ formed hydrogel polymer that is biocompatible and has a cure time after mixing of about 10 seconds to about 30 minutes and wherein the volume of said hydrogel polymer swells less than 30 percent after curing and hydration. Some embodiments of the inflation material may include radiopaque material such as sodium iodide, potassium iodide, barium sulfate, Visipaque 320, Hypaque, Omnipaque 350, Hexabrix and the like. For some inflation material embodiments, the polyglycidyl ether may be selected from trimethylolpropane triglycidyl ether, sorbitol polyglycidyl ether, polyglycerol polyglycidyl ether, pentaerythritol polyglycidyl ether, diglycerol polyglycidyl ether, glycerol polyglycidyl ether, trimethylolpropane polyglycidyl ether, polyethylene glycol diglycidyl ether, resorcinol diglycidyl ether, glycidyl ester ether of p-hydroxy benzoic acid, neopentyl glycol diglycidyl ether, 1,6-hexanediol diglycidyl ether, bisphenol A $(PO)_2$ diglycidyl ether, hydroquinone diglycidyl ether, bisphenol S diglycidyl ether, terephthalic acid diglycidyl ester, and mixtures thereof. For some inflation material embodiments, the diamine may be selected from (poly)alkylene glycol having amino or alkylamino termini selected from the group consisting of polyethylene glycol (400) diamine, di-(3-aminopropyl) diethylene glycol r, polyoxypropylenediamine, polyetherdiamine, polyoxyethylenediamine, triethyleneglycol diamine and mixtures thereof. For some embodiments, the diamine may be hydrophilic and the polyglycidyl ether may be hydrophilic prior to curing. For some embodiments, the diamine may be hydrophilic and the polyglycidyl ether is hydrophobic prior to curing. For some embodiments, the diamine may be hydrophobic and the polyglycidyl ether may be hydrophilic prior to curing.

Other inflation materials that may be used for some embodiments include polyethylene oxide materials and neopentyl glycol diacrylate materials which are discussed in U.S. Pat. Nos. 6,610,035 and 6,176,849, which are incorporated by reference herein in their entirety. U.S. Pat. No. 7,147,660, the contents of which are incorporated herein by reference, also includes inflation material embodiments that may be used for embodiments discussed herein.

Figure 3:
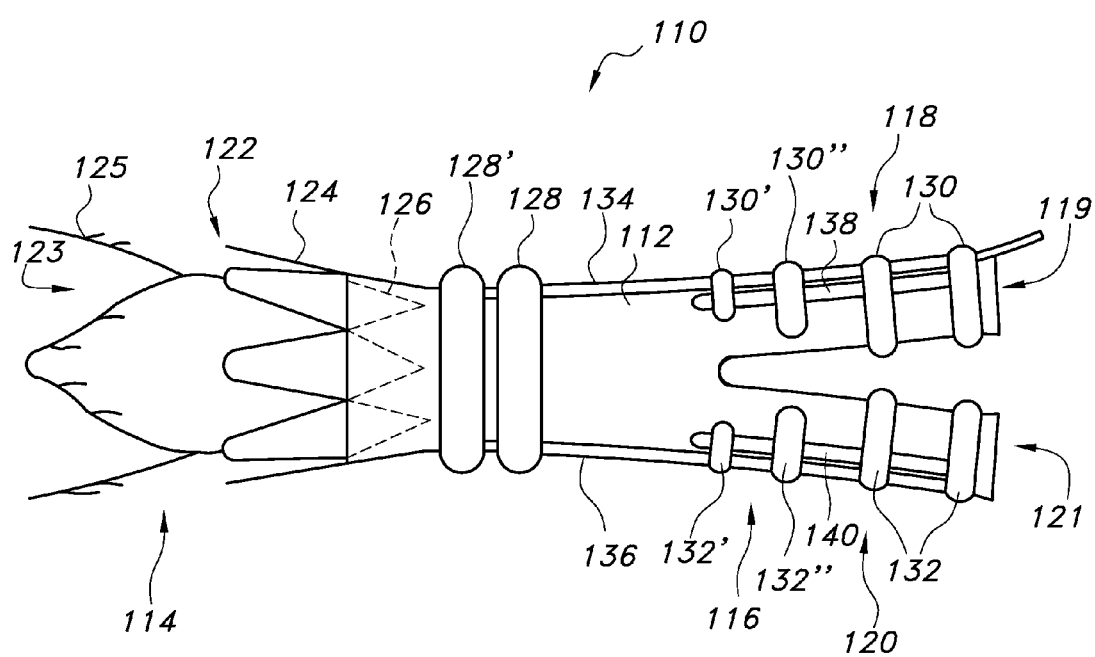
FIG. 3 is an elevation view of a bifurcated graft assembly useful for treating, but not limited to, abdominal aortic aneurysms according to the present invention.
Figure 4:
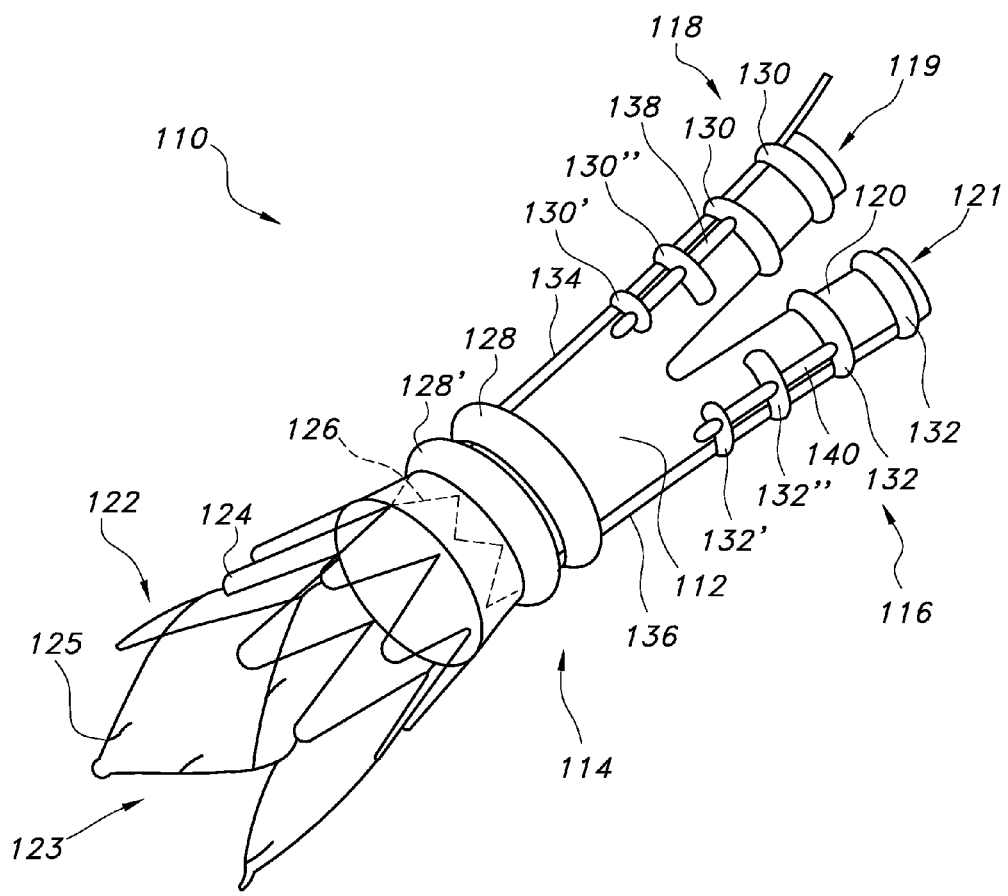
FIG. 4 is a perspective view of the graft assembly of FIG. 3.
Figure 5:
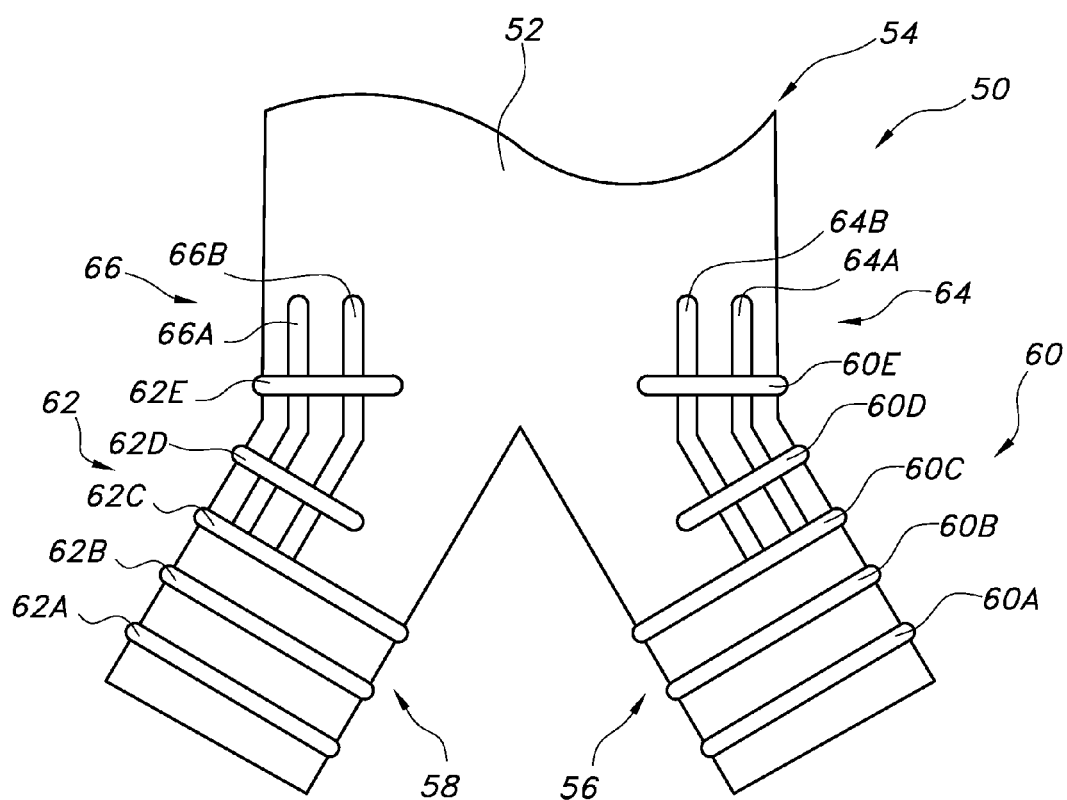
FIG. 5 is a close up view of one embodiment of a bifurcated region of a graft assembly according to the present invention.

FIGS. 3 through 5 show a bifurcated embodiment of a graft assembly 110 for treatment of an abdominal aortic aneurysm. The graft assembly 110 includes a bifurcated main graft member 112, having a proximal end 114 and distal end 116. At the distal end 116, the assembly 110 includes a bifurcated portion, including a first branched leg 118 (having a first leg lumen 119) and a second branched leg 120 (having a second leg lumen 121). In some embodiments, the first branched leg 118 may be referred to as an "ipsilateral leg" 118, and the second branched leg 120 may be referred to as a "contralateral leg" 120. The main graft 112 includes a tubular inner main fluid flow lumen 123 disposed therein. The lumen 123 extends from the proximal end 114 of the graft body 112 to the distal bifurcated region 116. The proximal end 114 includes a proximal anchor member 122, including a proximal stent 124 and proximal connector ring 126, as described above.

The proximal end 114 of the main body portion 112 includes at least one inflatable channel 128. The inflatable channel 128 located closest to the proximal end 114 may be considered an inflatable cuff (designated 128'). The first branched leg 118 includes at least one first branched circumferential inflatable channel 130, and the second branched leg 120 includes at least one second branched circumferential inflatable channel 132. The first branched leg 118 may include at least two first branched circumferential inflatable channels 130, and the second branched leg 118 includes at least two second branched circumferential inflatable channels 132. As explained above, the circumferential inflatable channels (including 128, 130, and 132) may extend the entire circumference of the graft body 112, first branched leg 118 or second branched leg 120, respectively, or may extend only a portion of the circumference. As depicted in FIGS. 3 and 4, the first branched circumferential inflatable channels 130 disposed furthest away from the proximal end 114 may extend the entire circumference of the first branched leg 118, while the first branched circumferential inflatable channels 130 disposed closest to the proximal end 114 may extend only a portion of the circumference of the first branched leg 118. A similar arrangement is desired for the second branched leg 120 and the second circumferential inflatable channels 132.

The first branched leg 118 of the main graft 112 has a first branched leg inflatable fill channel 134, which is in fluid communication with the first branched inflatable channels 130 and the proximal inflatable channel(s) 128. Similarly, the second branched leg 120 includes a second branched leg inflatable fill channel 136, which is in fluid communication with the second branched circumferential inflatable channels 132 and the proximal inflatable channel(s) 128. The main graft 112, first branched leg 118 and second branched leg 120 form a bifurcated "Y" shaped configuration.

The main fluid flow lumen 123 of the main graft 112 generally may have a larger transverse dimension and area than a transverse dimension and area of either of the leg lumens 119 and 121 (shown in FIG. 3) of the first branched leg 118 or second branched leg 120, respectively. A proximal anchor member 122 is disposed at a proximal end 114 of the main graft 112. The proximal anchor member 122 includes a proximal self-expanding stent 124 that is formed from an elongate element having a generally serpentine shape with four crowns or apices at either end, as explained above. A distal end of the proximal stent 124 may be mechanically coupled to a connector ring 126 which is embedded in graft material of the proximal end 114 of the main graft 112, or directly coupled to perforations in the proximal edge region of the main graft 112. Embodiments of the connector ring 126 may be generally circular in shape have regular undulations about the circumference that may be substantially sinusoidal in shape. The proximal stent 124 includes outwardly extending barbs 125, which may be integrally formed with the struts of the stent for some embodiments, having sharp tissue penetrating tips that are configured to penetrate into tissue of an inside surface of a lumen within which the proximal stent 124 is deployed in an expanded state. Although the proximal anchor member 122 is shown as including self-expanding stent 124, similar stents may be used that are configured to be inelastically expanded with outward radial pressure as might be generated by the expansion of an expandable balloon from within stent 124. The connector ring coupled to the proximal stent 124 may also be inelastically expandable.

In a desired embodiment, at least one of the first branched leg 118 and the second branched leg 120 includes at least two inflatable channels. Thus, the first branched leg 118 may include at least two inflatable channels 130, and the second branched leg 120 includes at least two inflatable channels 132. The inflatable channel (130, 132) which is disposed furthest from the proximal end 114 of the graft body 112 may serve as a cuff, as explained above. The inflatable channels 130, 132 may extend around the entire circumference of the leg 118, 120, or may extend only partially around the circumference. In one embodiment, as may best be seen in FIGS. 3 and 4, the inflatable channels 130, 132 which are located closest to the main body portion 112 (labeled 130', 130", 132' and 132") may only extend a portion of the circumference of the leg (118, 120, respectively). Such configuration allows for control while implanting and securing the graft 10 in a patient.

To provide added rigidity and stiffness to the device, it may be desirable to include a longitudinal channel between at least two inflatable channels. For example, first branched leg 118 may include at least two inflatable channels 130, with a longitudinal channel 138 disposed between at least two inflatable channels 130 and in fluid communication therewith. Similarly, second branched leg 120 may include at least two inflatable channels 132, with a longitudinal channel 140 disposed between at least two inflatable channels 132 and in fluid communication therewith. Longitudinal channels 138, 140 may be one channel or they may include a plurality of channels each in communication with adjacent circumferential inflatable channels (130, 132, respectively). It is desired to have a first longitudinal fill channel 134 extend along the first branched leg 118 to the proximal end 114 of the graft body 112, where the first longitudinal fill channel 134 is in fluid communication with the proximal circumferential inflatable channel(s) 128 and first inflatable channel(s) 130. Similarly, it is desired to have a second longitudinal fill channel 136 extend along the second branched leg 120 to the proximal end 114 of the graft body 112, where the second longitudinal fill channel 136 is in fluid communication with the proximal circumferential inflatable channel(s) 128 and second inflatable channel(s) 132. The use of longitudinal inflatable fill channels 134, 136 allow for controlled delivery of fluid to the various channels (including 128, 130, 132, 138 and 140).

FIG. 5 depicts an alternate embodiment of FIGS. 3 and 4, which includes a plurality of longitudinal channels connecting individual leg channels. In this embodiment, bifurcated graft assembly 50 includes a main graft portion 52 having a proximal end 54 and two branched legs 56, 58 opposite the proximal end 54. Each of the branched legs 56, 58 includes a series of circumferential inflatable channels. First branched leg 56 includes a series of first circumferential inflatable channels 60A through 60E. Each of the first circumferential inflatable channels 60A through 60E may extend the entire circumference of first branched leg 56, or may only extend around a portion of the circumference of first branched leg 56. The first circumferential inflatable channel(s) 60A through 60C located furthest from the proximal end 54 may extend the entire circumference of the first branched leg 56. Those channel(s) 60A (optionally 60B, 60C) located furthest from the proximal end 54 may be considered first leg cuff(s), as explained above. Similarly, second branched leg 58 includes a series of second circumferential inflatable channels 62A through 62E. Each of the second circumferential inflatable channels 62A through 62E may extend the entire circumference of second branched leg 58, or may only extend around a portion of the circumference of second branched leg 58. The second circumferential inflatable channel(s) 62A through 62C located furthest from the proximal end 54 may extend the entire circumference of the second branched leg 58. Those channel(s) 62A (optionally 62B, 62C) located furthest from the proximal end 54 may be considered first leg cuff(s), as explained above.

Each of the first branched leg 56 and second branched leg 58 thus includes a series of inflatable channels (generally 60, 62, respectively). To add rigidity and strength to the device during use, it may be desirable to include at least one longitudinal channel between at least two inflatable channels and in fluid communication therewith. Thus, in this embodiment, there may be at least one first longitudinal channel 64 between at least two first circumferential inflatable channels 60, and there may be at least one second longitudinal channel 66 between at least two second circumferential inflatable channels 62. For example, first branched leg 56 may include first circumferential inflatable channels 60C through 60E, which are connected by and in fluid communication with second longitudinal inflatable channels 64A, 64B. Again, similarly, second branched leg 58 may include second circumferential inflatable channels 62C through 62E, which are connected by and in fluid communication with second longitudinal inflatable channels 66A, 66B. Any number of circumferential inflatable channels (60, 62) may be used, and any number of longitudinal inflatable channels (64, 66) may be used. Each leg 56, 58 may include between 2 and 8 circumferential inflatable channels (60, 62), and each leg 56, 58 includes between 1 and 4 longitudinal inflatable channels (64, 66).

Figure 6:
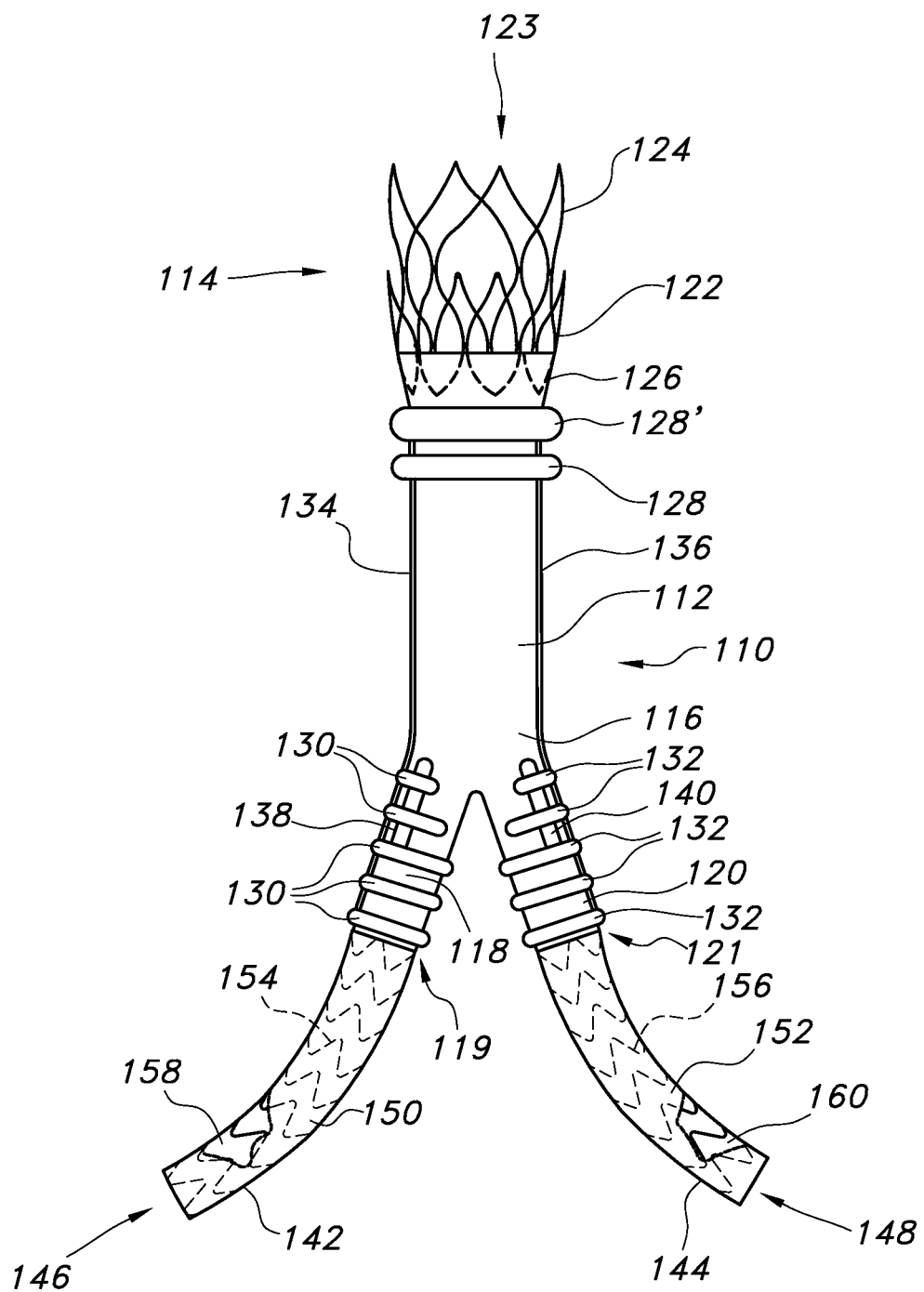
FIG. 6 is an elevation view of a modular bifurcated graft assembly useful for treating, but not limited to, abdominal aortic aneurysms according to the present invention.

FIG. 6 depicts a modular bifurcated graft assembly 110, which generally includes the bifurcated assembly described above (in FIGS. 3 through 4), but includes optional first and second graft extensions 142, 144. As with the assembly described above, modular bifurcated graft assembly 110 includes a generally tubular main graft body 112, which has a proximal end 114 and distal end 116, with first and second branched legs 118, 120 disposed at the distal end 116. The assembly 110 includes a generally tubular lumen 123 extending through the main graft portion 112 to the bifurcated region and through the lumens (119, 121) of the first and second branched legs 118, 120. The proximal end 114 may include an anchoring device 122, a proximal stent 124, and proximal connector ring 126 connecting the main graft body 112 with the proximal stent 124. The proximal end 114 of the main graft body portion 112 may include one or more proximal circumferential inflatable channel(s) 128, 128'. As with above, the proximal circumferential inflatable channel 128 disposed closest to the proximal end 114 may be considered an inflatable cuff.

Each of the first and second branched legs 118, 120 includes a series of circumferential inflatable channels (first circumferential inflatable channels 130 and second circumferential inflatable channels 132). Any number of circumferential inflatable channels (130, 132) may be used and, as explained above, individual circumferential inflatable channels (130, 132) may extend either the entire circumference of their respective leg (118, 120) or only partially around the circumference. In a desirable embodiment, each leg (118, 120) includes at least two circumferential inflatable channels (130, 132), respectively. It may be desirable to include a first inflatable fill channel 134, which extends along the first branched leg 118 to the proximal end 114 of main graft body 112, and which is in fluid communication with each of the first circumferential inflatable channel(s) 130 and proximal inflatable channel(s) 128. Similarly, it may be desirable to include a second inflatable fill channel 136, which extends along the second branched leg 120 to the proximal end 114 of main graft body 112, and which is in fluid communication with each of the second circumferential inflatable channel(s) 132 and proximal inflatable channel(s) 128'.

To provide added rigidity and support to the device, it may be desirable that each leg (118, 120) includes a longitudinal inflatable channel between at least two circumferential inflatable channels. Thus, first branched leg 118 may include a first longitudinal inflatable channel 138, which is between and in fluid communication with at least two first circumferential inflatable channels 130. Similarly, second branched leg 120 may include a second longitudinal inflatable channel 140, which is between and in fluid communication with at least two second circumferential inflatable channels 132.

Modular bifurcated graft assembly 110 may include one or two stent graft extensions 142, 144. The first graft extension 142 has a first fluid flow lumen 146 disposed therein. The first graft extension 142 has an outer surface which may be sized and configured to be sealed to an inside surface of the first branched leg 118 of the main graft 112 with the inner fluid flow lumen 146 of the first graft extension 142 in fluid communication with the fluid flow lumen of the first branched leg 118. Typically, an outside surface 150 of the first graft extension 142 may be sealed to an inside surface of the first branched leg 118 of the main graft 112 when the first graft extension 142 is in a deployed state. Similarly, the second graft extension 144 has a fluid flow lumen 148 disposed therein. The second graft extension 144 has an outer surface 152 which may be sized and configured to be sealed to an inside surface of the second branched leg 120 of the main graft 112 with the second fluid flow lumen 148 in fluid communication with the fluid flow lumen of the second branched leg 120. Typically, an outside surface 152 of the second graft extension 144 may be sealed to an inside surface of the second branched leg 120 of the main graft 112 when the second graft extension 144 is in a deployed state.

For some embodiments, the axial length of the first and second branched legs 118 and 120 may be sufficient to provide adequate surface area contact between outer surfaces 150 and 152 of first and second graft extensions 142 and 144. Additionally, the respective inside surfaces of the first and second branched legs 118 and 120 should provide sufficient friction to the first and second outer surfaces 150, 152 to hold the first and second graft extensions 142 and 146 in place. Expandable members, such as expandable anchor members and the like, may be used to expand the graft extensions 142 and 144 against the inside surfaces of the fluid flow lumens of the first and second branched legs 118 and 120. Varying the amount of overlap between the legs and extensions can allow for different effective overall graft lengths to be achieved, thereby accommodating a range of anatomical sizes with fewer distinct main body and extension dimensions than would otherwise be required. For some embodiments, the first and second branched legs 118 and 120 may have an axial length of at least about 1 cm. For some embodiments, the first and second branched legs 118 and 120 may have an axial length of about 2 cm to about 6 cm, more specifically, about 3 cm to about 5 cm.

Some embodiments of main graft member 112 may include about 1 to about 8 circumferential inflatable channels 130,132 disposed about each leg 118, 120 and about 1 to about 8 proximal circumferential channels 128 disposed about a main body portion of the main graft member 112. Some embodiments of the main graft body member 112 may include about 1 to about 4 longitudinal or axial inflatable fill channels 134, 136 that may serve to connect the circumferential inflatable channels (128, 130, 132). Some embodiments of the circumferential channels may extend a full circumference of the graft section upon which they are disposed, or they may extend only partially around the graft section upon which they are disposed. For the main graft member embodiment 112 shown in FIG. 6, the network of proximal inflatable channels 128, 128' includes an inflatable cuff 128' disposed adjacent the proximal end 114 of the main body portion 112 and a circumferential channel 128 disposed just distal of the inflatable cuff 128'. Each leg 118 and 120 of the main graft member 112 includes 3 complete circumferential inflatable channels 130, 132 in axial series. Each leg 118 and 120 of the main graft member 112 also has two partial circumferential inflatable channels 130, 132 disposed proximally of the complete circumferential inflatable channels 130, 132.

For some method embodiments of treating the vasculature of a patient, a modular graft assembly, such as the modular graft assembly embodiments 110 discussed above, may be used. Various methods of delivery systems and delivery of the device into a patient include those described in Applicant's co-pending application, U.S. Patent Application Publication No. 2009/0099649, the contents of which are incorporated by reference in entirety herein. For endovascular methods, access to a patient's vasculature may be achieved by performing an arteriotomy or cut down to the patient's femoral artery or by other common techniques, such as the percutaneous Seldinger technique. For such techniques, a delivery sheath (not shown) may be placed in communication with the interior of the patient's vessel such as the femoral artery with the use of a dilator and guidewire assembly. Once the delivery sheath is positioned, access to the patient's vasculature may be achieved through the delivery sheath which may optionally be sealed by a hemostasis valve or other suitable mechanism. For some procedures, it may be necessary to obtain access via a delivery sheath or other suitable means to both femoral arteries of a patient with the delivery sheaths directed upstream towards the patient's aorta. In some applications a delivery sheath may not be needed and a delivery catheter may be directly inserted into the patient's access vessel by either arteriotomy or percutaneous puncture.

Figure 7:
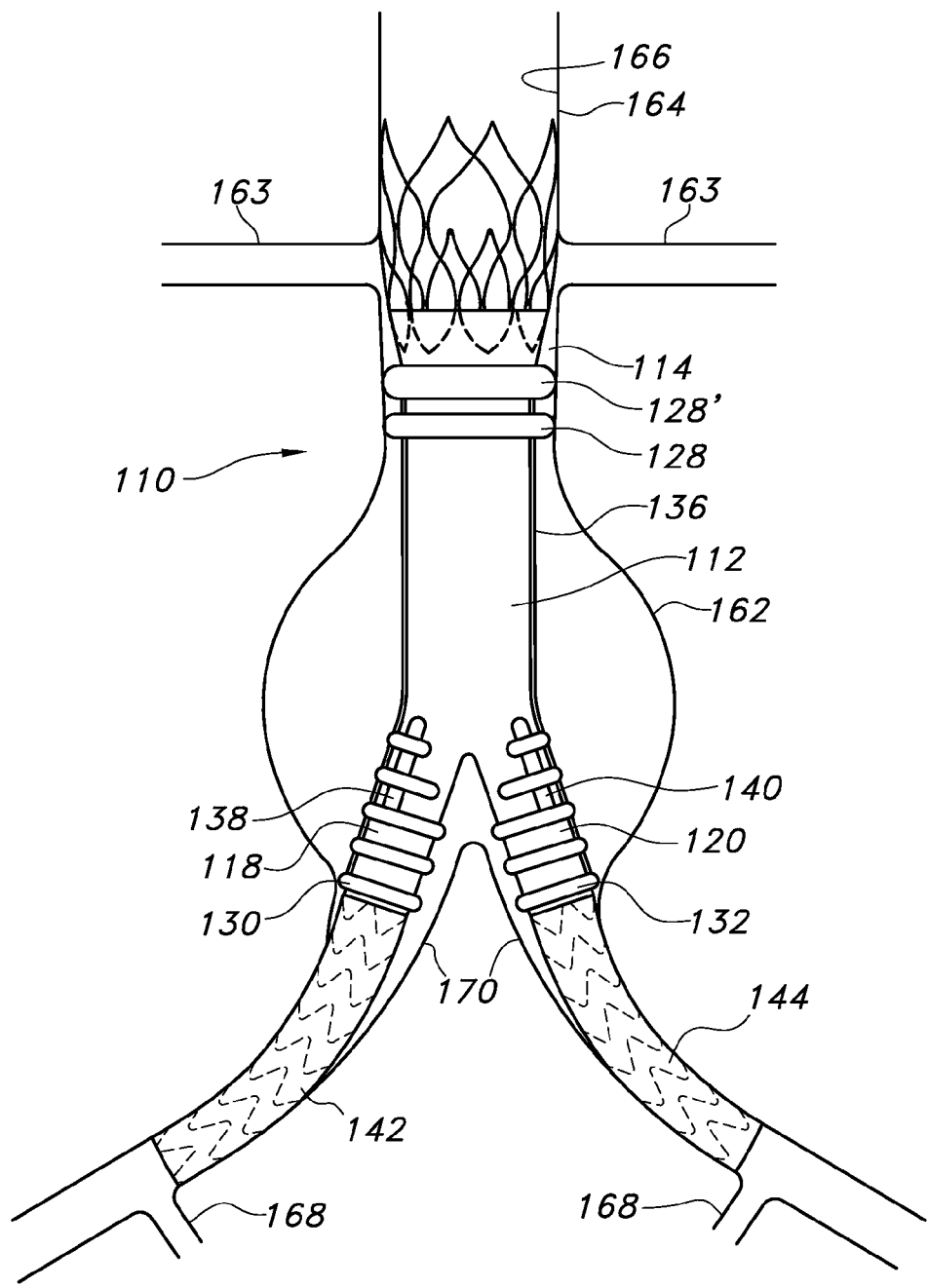
FIG. 7 depicts the assembly of FIG. 6 in its implanted state.

FIG. 7 depicts the assembly of FIG. 6 in a deployed state. As can be seen, in its deployed state, the modular bifurcated graft assembly includes a first and second stent graft extension 142, 144 disposed in the first and second branched legs 118, 120. The main body portion 112 and first and second branched legs 118, 120 span or substantially span the diseased region of abdominal aorta or aneurysm 162, providing safe passage therethrough. The proximal end 114 of the main graft body 112 engages the inner wall 166 of the aorta 164 near, and typically prior, the renal arteries 163. A portion of the anchoring device 122 may bridge the renal arteries 163. As can be seen, in this embodiment, the proximal circumferential inflatable channel 128' acts as a cuff, holding the assembly 110 in place. The first and second stent graft extensions 142, 144 may extend from above the hypogastric arteries 168 and into and/or through the iliac arteries 170.

The first and second graft extensions 142 and 144 may be formed from an inner layer or layers and outer layer or layers of flexible graft material, such as PTFE or ePTFE. In one embodiment, the flexible graft material includes PTFE which is substantially porous but includes no discernable node and fibril structure. The inner and outer layers of graft material may be formed from tubular extrusions, laminated wraps of multiple layers of graft material or materials, and the like. The inner or outer layers of graft material may be permeable, semi-permeable or substantially non-permeable for some embodiments. For some embodiments, the nominal length of the extensions 142 and 144 may be permeable with one or more longitudinal sections, such as a middle longitudinal section, being semi-permeable or non-permeable. Some embodiments of the graft extensions 142 and 144 may have an overall tapered or flared configuration with a nominal inner lumen that tapers or flares when the graft extension is in a relaxed expanded state. For embodiments that include laminated wraps of material, the wraps may be carried out circumferentially, helically or in any other suitable configuration.

The first and second leg extensions 142, 144 are desirably stent-graft devices. A first radially expandable stent 154 may be interposed between an outer layer 150 and inner layer 158 of graft material. A second radially expandable stent 156 may be interposed between an outer layer 152 and inner layer 160 of graft material. The interposed stent 154, 156 disposed between the outer layer 150, 152 and inner layer 158, 160, respectively, of graft material may be formed from an elongate resilient element helically wound with a plurality of longitudinally spaced turns into an open tubular configuration. The helically wound stent 154, 156 may be configured to be a self-expanding stent or radially expandable in an inelastic manner actuated by an outward radial force from a device such as an expandable balloon or the like. Some tubular prosthesis embodiments that may be used for graft extensions 142 and 144 are discussed in U.S. Pat. No. 6,673,103 to Golds et al., titled "Mesh and Stent for Increased Flexibility", which is hereby incorporated by reference in its entirety herein.

The graft extensions 142 and 144 may optionally include attachment elements disposed on outer surfaces 150, 152 of their respective proximal ends or sections that may be used to couple to corresponding attachment elements disposed on inside surfaces of the respective first branched leg 118 and second branched leg 120 of the main graft 112. Attachment element embodiments that may be used on outside surfaces 150 and 152 of the graft extensions 142 and 144 and inside surfaces of first and second branched legs 118 and 120 of the main graft 112 may include any of the attachment elements in U.S. Patent Application Publication No. 205/0228484, entitled "Modular Endovascular Graft", by Stephens, et al., which is hereby incorporated by reference herein in its entirety. The first graft body section may have a first wall portion and a first attachment element disposed on the first wall portion and the second graft body section may have a second attachment element disposed on a second wall portion of the second graft body section. The second attachment element may be configured to be secured to the first attachment element with respective fluid flow lumens of the first and second graft body sections sealed together. For some embodiments, the first and second attachment elements may be secured together in an overlapped portion of the first and second graft body sections. For some embodiments, the first attachment element may include a plurality of flexible hooks and the second attachment element includes a plurality of flexible loops adjacent each other wherein the flexible hooks are configured to mechanically engage the flexible loops when the first and second attachment elements are pressed together. For some embodiments, the first attachment element includes a plurality of buttons having an enlarged head portion regularly spaced from each other on a surface a first wall portion and a second attachment element includes an expandable mesh having a plurality of apertures configured to allow entry of the enlarged head portion of the buttons while the mesh is in a circumferentially constrained state and to capture the enlarged head portion of the buttons when the mesh is in a circumferentially expanded state. For some embodiments, the first attachment element includes a plurality of pins radially extending from a surface of a first wall portion and the second attachment element includes an expandable mesh having a plurality of apertures configured to allow entry of the pins when the first attachment element is pressed against the second attachment element. For some embodiments the first attachment element may include an inflatable cuff containing curable material and the second attachment element includes an expandable member with barbs configured to extend outwardly into the inflatable cuff and curable material.

Graft extensions 142 and 144, which may be interchangeable for some embodiments, or any other suitable extension devices or portions of the main graft section 112 may include a variety of suitable configurations. Alternatively, the graft extensions 142, 144 may be useful as a separate endovascular stent graft, apart from the bifurcated graft assembly 110. For some embodiments, graft extensions 142 and 144 may include a PTFE covered helical nitinol stent 154, 156 as discussed above with layers of PTFE having a variety of characteristics. Regarding the stent 154, 156, it may be formed from an elongate resilient element which is helically wound with a plurality of longitudinally spaced turns.

Some stent embodiments may be generally helical in configuration with serpentine or other regularly spaced undulations transverse to the helical path of the elongate stent element as shown in more detail in FIGS. 8 through 11. As can be seen, a generally tubular stent 300 may be provided. The tubular stent 300 includes a helically-wound, undulating wire forming a series of adjacent helical windings 302, which may be made from the materials described above (including a resilient metal such as nitinol). The ends 304, 306 of the stent 300 may be secured to adjacent ring portions of the stent at distinct areas. For example, a first end may be adjoined via a first securement point 308, and a second end may be joined at a second securement point 310, as shown to avoid exposure of element ends to either PTFE graft material or possible patient tissues. In a preferred embodiment, the securement points 308, 310 are located proximal to the first end 304 and second end 306, respectively, with no other securement points on the stent 300. That is, aside from the helical windings 302 at the first end 304 and second end 306, respectively, adjacent approximate circumferential windings 302 in the stent 300 may be free of interconnecting securement points. Any securement means may be used, including, for example, welding, such as struts and welds. It is desired that the relative stiffness of a stent be greater than the stiffness of the PTFE graft material so as to provide beneficial kink resistance.

The undulating wire may be a continuous element forming a series of helical windings 302 extending from one end 304 of the extension to the other end 306 thereof. The tubular stent 300 thus has an internal lumen 320 extending therethrough, from the first end 304 to the second end 306. The ends 304, 306 of the elongate element may be secured to adjacent ring members by any suitable means such as adhesive bonding, welding such as laser welding, soldering or the like. For some embodiments, the stent element may have a transverse dimension or diameter of about 0.005 inch to about 0.015 inch. As may be seen in FIGS. 9A and 9B, the stent 300 may be tapered or flared. In addition, if desired, adjacent helical windings 302 may be arranged 315 such that adjacent helical windings 302 at one end (either the first end 304 or second end 306) have an acute angle formation at a portion of the stent 300 proximal to the end of the stent 300. That is, if desired, the helical winding closest to the end (shown as 302') may have an approximately 180° angle with respect to the longitudinal axis, while the helical winding next to this helical winding (shown as 302") has an angle less than 180°. These two helical windings (302' and 302") may be attached at securement points 308, 310.

Figures 10A, 10B:
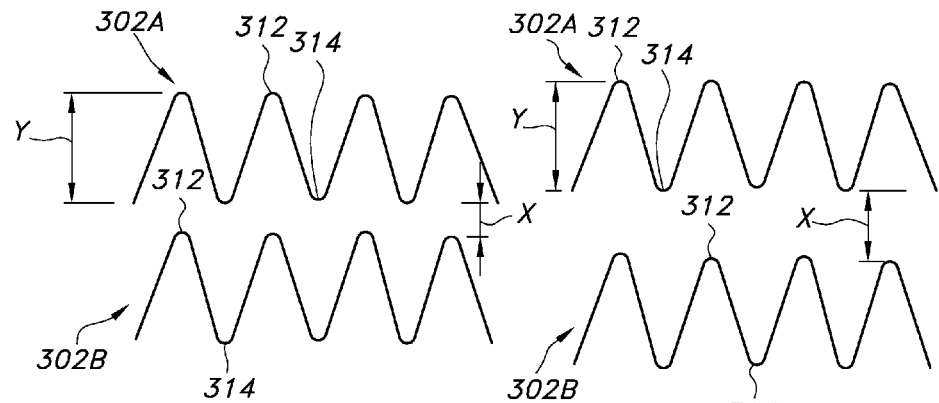
FIGS. 10A through 10E depict various arrangements of helically wound stents of the present invention.
Figures 10C, 10D:
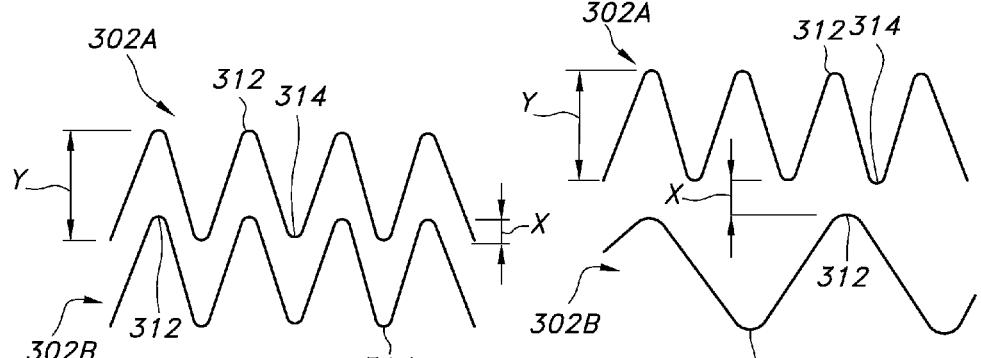
Figure 10E:
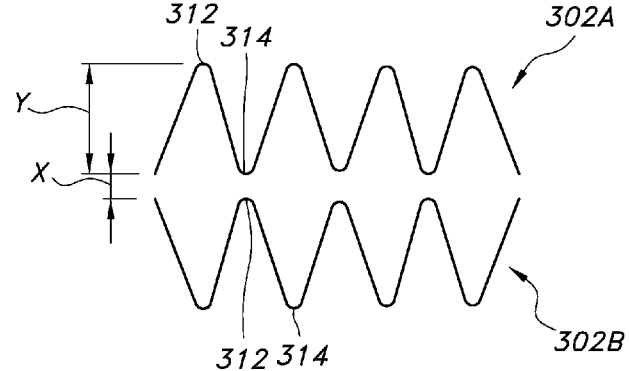

FIG. 10A through 10E depicts various arrangements of the helical windings 302 formed by the undulating wire in forming the stent 300. Adjacent helical windings are depicted as 302A and 302B, but it will be understood that the arrangement depicted in FIGS. 10A through 10E may be applied to each helical winding 302 in the stent 300. Alternatively, the arrangements depicted in FIGS. 10A through 10E may be applied to only some of the helical windings 302 in the stent 300. Undulating wire of the stent 300 includes a series of peaks 312 and valleys 314 as the wire is helically wound. The arrangement of peaks 312 and valleys 314 may vary and may be arranged in any fashion desired. In some embodiments, such as that of FIG. 10A, the peaks 312 of one circumferential winding 302A may be substantially aligned with the peaks 312 of an adjacent circumferential winding 302B. As can be seen in FIG. 10B, the adjacent circumferential windings 302A and 302B may be spaced apart. As can be seen in FIG. 10C, the adjacent circumferential windings 302A and 302B may be closer together. In another embodiment, set forth in FIG. 10D, one peak 312 of one circumferential winding 302B may span two peaks 312 of an adjacent winding 302A. In another embodiment set forth in FIG. 10E, the peaks 312 of one circumferential winding 302A may be substantially aligned with the valleys 314 of an adjacent circumferential winding 302B. Other arrangements for the helical windings 302 are contemplated and will be readily understood by those of skill in the art.

The distances between adjacent windings 302A, 302B may vary along the length of the stent 300, where the distance at one end 304 is different than the distance at the second end 306. In each embodiment, there are two distances that should be considered. The first distance X is the distance between the lowest valley (314) of the first winding (302A) and the highest peak (312) of the second winding (302B). The second distance Y is the distance between the highest peak (312) and lowest valley (314) of the first winding (302A).

There may be at least two different ratios of X/Y (or equivalently X/Y) present in the device, including but limited to three different relative ratios of these distances X/Y. The first ratio is where X/Y is a relatively large positive number, that is, there is a relatively larger separation between the distance (X) as compared to the distance (Y). The second ratio is where X/Y is a relatively smaller positive number, that is, there is a relatively smaller separation between the distance (X) as compared to the distance (Y). Finally, the third ratio is where X/Y is a negative number, that is, the lowest peak of the first winding (302A) dips to a point lower than the highest peak of the second winding (302B). An example of a negative ratio is seen in FIG. 10C, where a negative value for X can be seen.

The ratio X/Y can be manipulated to obtain the desired properties of the stent graft in a local region. A relatively large X/Y ratio (preferably greater than about 0.5) produces a highly flexible region of a stent graft. A smaller X/Y ratio (preferably from about 0.1 to about 0.5) produces regions of a stent graft with moderate flexibility and moderate radial force. A region of a stent graft with an even smaller or negative X/Y ratio (preferably less than about 0.1) has a relatively high radial force with relatively less flexibility. The above ranges for X/Y are appropriate when the stent height Y is from about one-third of the diameter of the stent to about equal to the diameter of the stent. If Y is larger than this when compared to D, then the ranges for the X/Y ratios quoted above will be reduced. Similarly, if Y is much smaller than the stent diameter D, then the numerical values for the ranges above will be increased.

Using the principle described above, a stent graft can be constructed with varying ratios of X/Y along the length to achieve desired properties. For example, if a stent graft is used as an iliac limb in a modular endovascular graft for abdominal aortic aneurysms (AAAs), it may be desirable for the proximal end of the stent graft to have a relatively high radial force to maximize anchorage into the aortic body component of the modular system. In this case, the proximal end of the iliac limb could be designed with a small or negative X/Y ratio, such as −0.5, and Y may be chosen to be, for example, from about one fifth to one half of the stent graft diameter. In this region flexibility is less important than radial force so the negative X/Y ratio yields the desired properties. In the middle of the stent graft flexibility becomes important to accommodate the tortuous common iliac arteries often found in AAA patients. It may then be desirable to have a relatively large X/Y ratio, such as about 0.55, to achieve this flexibility. Near the distal end of the stent graft it may again be desirable to have more radial force to promote anchorage and sealing of the iliac limb into the common iliac artery of the patient, but not as much radial force as at the proximal end. In this case, it may be desirable to have an X/Y ratio near zero, or from about −0.1 to about 0.3.

Since the stent is formed in a helix along the length of the stent graft, it is possible to continuously vary the X/Y ratio to achieve the desired properties in various regions of the stent graft with smooth variations and no abrupt changes along the length. These smooth variations promote conformance to the vasculature and avoid the stress and/or strain concentrations and potential kinking that can result from abrupt transitions in mechanical properties along the length of a stent graft.

Figures 9A, 9B:
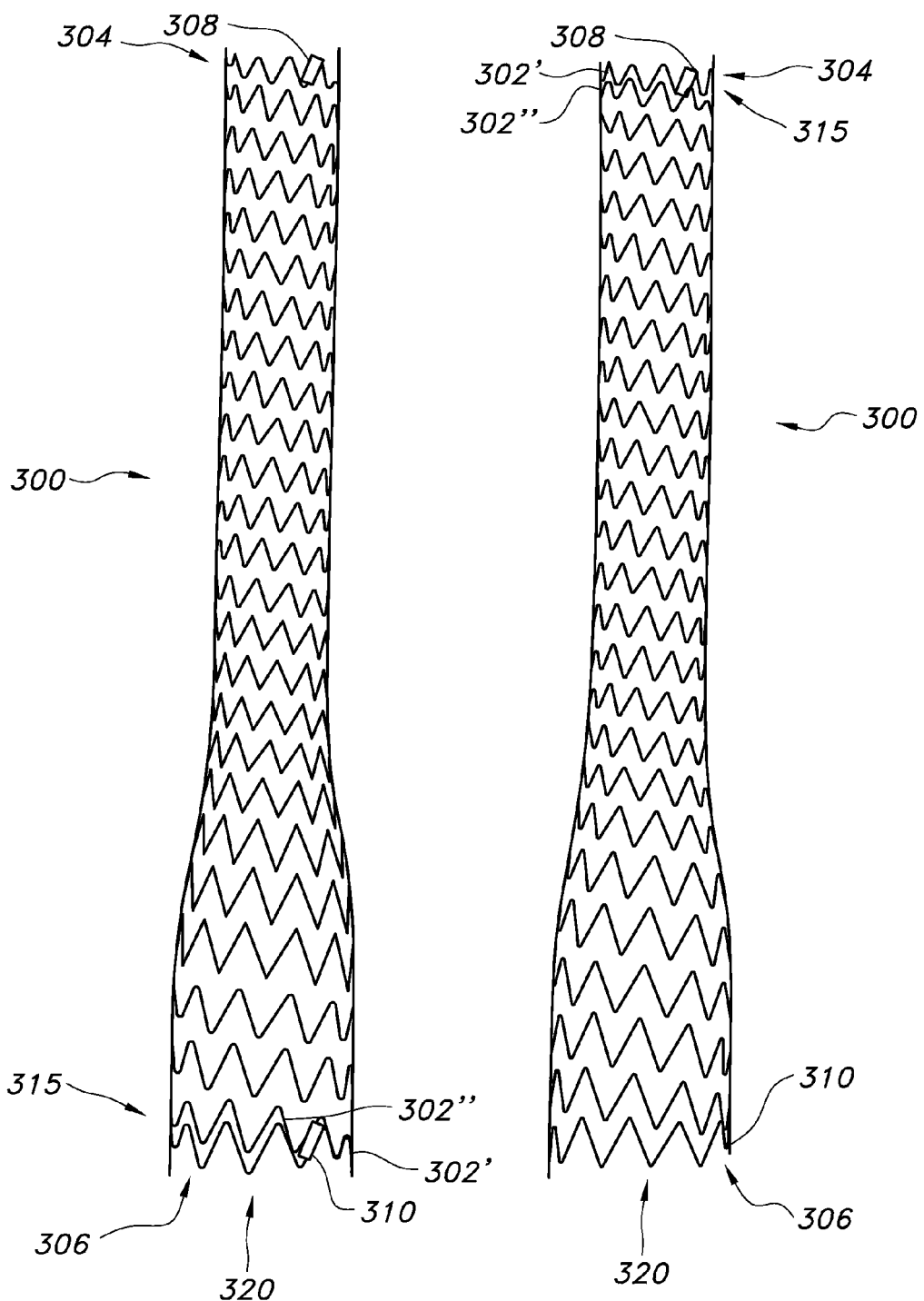
FIGS. 9A and 9B depict various embodiments of stent structures useful in the present invention.

The stent 300 may include a longitudinal axis (generally defined along internal lumen 320) and a radial axis perpendicular to the longitudinal axis; where the helical windings 302 are wound at an acute winding angle of about 3 degrees to about 15 degrees with respect to the radial axis. As can be seen in FIGS. 9A and 9B, the acute winding angle at a portion of the stent 300 proximal to the first end 304 is different from the acute winding angle at a portion of the stent 300 proximal to the second end 306. In some embodiments, a first helical winding 302 at the first end 304 may be perpendicular to the longitudinal axis. Further, it may be desired that a helical winding 302 at the second end 306 is perpendicular to the longitudinal axis. Helical windings 302 at the first end 304 and the second end 306 may both be perpendicular to the longitudinal axis, or only one may be perpendicular to the longitudinal axis. An adjacent peak 312 and an adjacent valley 314 of a helical winding 302 have a peak height from an apex of said adjacent peak to a base of said adjacent valley. It may be desired that the peak height at a portion of the stent 300 proximal to the first end 304 of the stent 300 is different from the peak height at a portion of the stent 300 proximal to the second end 306 of the stent 300.

At least one graft layer may be disposed on the stent 300. The placement of the graft layers may best be seen in FIGS. 11A through 12. In some embodiments, an inner graft layer 318 may be disposed on the interior surface of the helically wound stent 300, forming inner lumen 320. A second graft layer 316 may be disposed on the outer surface of the helically wound stent 300, forming an outside surface. More than one or two layers of graft material may be disposed on the interior or exterior of the helically wound stent 300 as desired. For some embodiments of first or second graft extensions 142, 144, layers of materials having different properties may be used in combination to achieve a desired clinical performance. For example, some layers of PTFE covering the stent 300 may be permeable, semi-permeable or substantially non-permeable depending on the desired performance and material properties. The layers 316 and 318 may be applied by a variety of methods and have a variety of configurations. For example, some layer embodiments may include extruded tubular structures applied axially over a mandrel or subassembly. Some layer embodiments 316 and 318 may be applied by wrapping layers circumferentially or wrapping tapes or ribbons in an overlapping helical pattern. For some embodiments, the outer layer 316 may be made from or include a semi-permeable or substantially non-permeable PTFE layer and the inner layer 318 may be made of or include a permeable layer of PTFE.

The first and/or second graft extensions 142, 144 may be made by forming the layers of material 316, 318 together with the helically wound stent 300 over a mandrel, such as a cylindrical mandrel (not shown). Once the innermost layer 316 of the extension 142, 144 has been wrapped about a shaped mandrel, a helical nitinol stent, such as helical stent 300, may be placed over the innermost layered PTFE layer 316 and underlying mandrel. If desired, one or more additional layers 318 of graft material may be wrapped or otherwise added over the exterior of the stent 300. If desired, the outer layer 318 may include low permeability PTFE film or PTFE film having substantially no permeability that does not have the traditional node fibril microstructure. The mandrel may then be covered with a flexible tube such that the layers 316, 318 and stent 300 are sandwiched under pressure and sintered so as to raise the temperature for the PTFE material to undergo a melt transformation in order to lock in its geometry and strength. The flexible tube (a manufacturing aid not shown) is removed from over the device and the resultant graft extension (142, 144) is removed from the mandrel.

Figure 13:
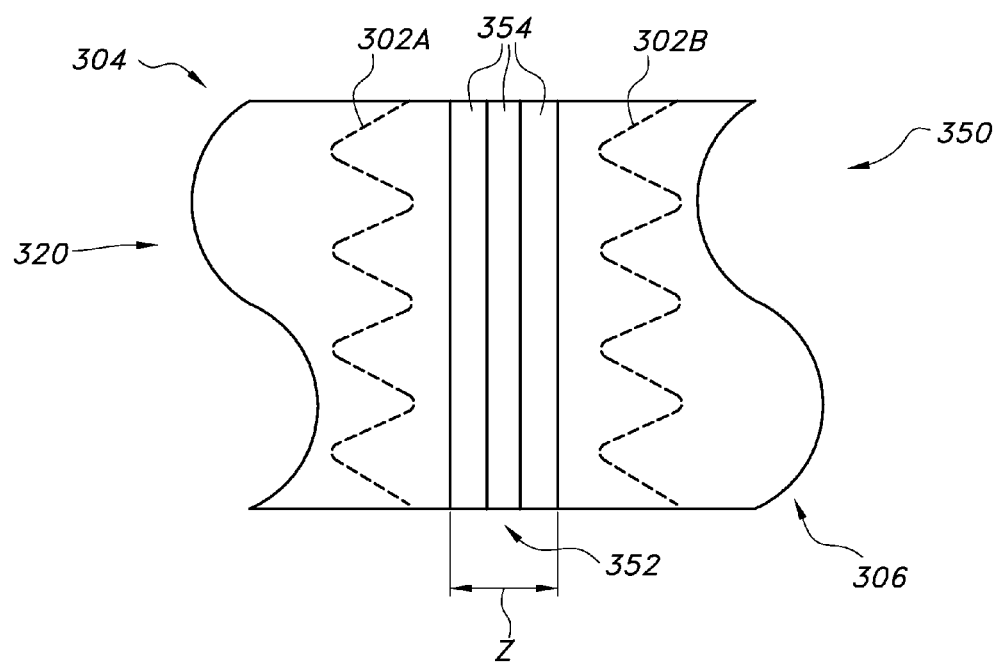
FIG. 13 is a close up view of one section of a crimped stent graft of the present invention.
Figure 14:
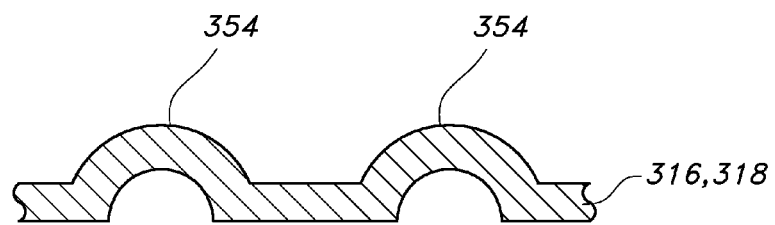
FIG. 14 is a cross sectional view of a crimped section of a crimped stent graft useful in the present invention.

It may be desirable to include at least one series of crimps in the graft material for one or both graft extensions 142, 144. As depicted in FIGS. 13 and 14, a crimped stent graft 350 may be formed. The crimped stent graft 350 includes a helically wound stent 300 described above having a first end 304 and a second end 306 and tubular lumen 320 extending therebetween, with at least one layer of graft material disposed thereon. Both an interior layer 318 and exterior layer 316 of graft material may be disposed on the stent 300. The crimped stent graft 350 includes at least one crimped region 352 disposed between at least two adjacent windings 302A, 302A. The crimped region 352 may extend as long as the space between adjacent windings 302A, 302B. Alternatively, the crimped region 352 may extend only as long as a portion of the space between adjacent windings 302A, 302B. The length of the crimped region is designated by the line depicted as Z on FIG. 13. The crimped region 352 includes a plurality of crimps 354, which are portions of graft material which have been compressed and form a crimping configuration. The crimped stent graft 350 may include a crimped region 352 between each adjacent winding 302A, 302B of the stent 300. The crimps 354 may extend around the entire circumference of the crimped stent graft 350, or may extend only a portion of the circumference of the crimped stent graft 350. As can be seen in FIG. 14, the crimps 354 may have a generally semi-circular configuration.

The crimped stent graft 350 may be formed through any desired means. In one embodiment, the crimped stent graft 350 is formed through a first method. This first method includes the steps of forming a generally tubular, helically wound stent 300 as described above. The helically wound stent 300 is then axially stretched, forming an axially stretched helically wound stent. A first graft liner is disposed on the interior lumen 320 of the helically wound stent 300, thus forming a first graft layer 318. The first graft layer 318 may be disposed before the stent 300 is placed on a mandrel or after the stent 300 is placed on a mandrel. The first graft layer 318 may then be attached to the stent 300. The first graft layer 318 may be made of porous PTFE having no discernable node and fibril structure, but may be made from other materials as described above. A discernable node and fibril structure may be observed and/or measured through the use of a scanning electron microscope (SEM). Porous PTFE of the present invention may have no discernable node and fibril structure even at about 20,000× (20,000 times) magnification under SEM or the like. Such magnification is not limiting and other magnifications, such as 10,000× or greater may be used. A graft covering is then disposed on the outer surface of the axially stretched tubular stent 300, the graft covering thus forming a second graft layer 316. Again, the second graft layer 316 may be made of porous PTFE having no discernable node and fibril structure, but may be made from other materials as described above. The second graft layer 316 may be attached to the stent 300 via any desired means. Finally, the axially stretched tubular stent 300 is allowed to relax, forming a crimped region 352 including a plurality of crimps 354 in the first graft layer 318 and second graft layer 316.

Another method to form a crimped stent graft 350 is provided herein. This alternative embodiment includes providing a tubular stent 300, the tubular stent 300 having an inner surface (i.e., a lumen 320 extending therethrough) and an outer surface. The stent may include an undulating wire having opposed first and second ends and being helically wound into a plurality of approximate circumferential windings 302 to define a stent wall. Further, the undulating wire may have a plurality undulations defined by peaks 312 and valleys 314 with peaks of adjacent approximate circumferential windings 302 being separated by a desired distance. As described above, the distance between adjacent windings 302 may be any desired distance, and in particular is most desirably the distance explained above. A graft liner is disposed on the inner lumen 320 of the tubular stent, forming a first graft layer 318. The first graft layer 318 may be made from porous PTFE having no discernable node and fibril structure, or alternatively may be made from other biocompatible materials described above. A graft covering may then be disposed on the outer surface of the tubular stent 300, forming a second graft layer 316. As with the first graft layer 318, the second graft layer 316 may be made from porous PTFE having no discernable node and fibril structure, but may be made from any materials described above. The tubular stent 300, first graft layer 318 and second graft layer 316 are disposed on a shaped mandrel (not shown), the shaped mandrel including at least one crimp shape on its outer surface. The crimp shape may be aligned so that the crimp shape is disposed between adjacent helical windings 302 of the stent 300. Then, the assembly may be heated and sintered, thus forming a crimped stent graft 350 including at least one crimp region 352 including a plurality of crimps 354. The crimps 354 of the crimped region 352 will generally conform to the crimp shape of the shaped mandrel.

In addition, for some embodiments, an adhesive such as FEP or the like may be applied adjacent the stent 300 prior to the application of the PTFE layer(s) covering the stent, or at any other suitable time or location, in order to facilitate a bond between the stent element and the PTFE materials adjacent the stent 300. For some embodiments, the permeable PTFE material 318 may include an ePTFE material having uniaxial expansion with a uniaxial node fibril structure. PTFE materials having a multiaxial node fibril orientation may also be used for some embodiments. For some embodiments, the permeable material may include about 1 to about 5 layers of material or more and have an inter nodal distance of about 10 microns to about 30 microns. The permeable material may have a thickness for some embodiments of about 0.00005 inch to about 0.005 inch.

For some embodiments, the low permeability non-expanded PTFE material may have a non-typical node fibril microstructure with essentially no nodal spacing and very low or no liquid permeability. The extensions 142, 144 may include about 1 layer to about 5 layers of semi-permeable or substantially non-permeable PTFE material having a thickness of about 0.0001 inches to about 0.005 inches, more specifically, about 0.0004 inches to about 0.001 inches. Examples of such materials are described in U.S. Patent Application Publication Nos. 2006/0233990 and 2006/0233991 described above which are incorporated by reference in their entirety herein.

For some embodiments, the PTFE material having low permeability or substantially no permeability may be made by providing a PTFE layer and applying a stretching agent, such as isoparaffinic fluids, such as those sold under the brand name Isopar™ by ExxonMobil Chemical Co., to at least a portion of the PTFE layer and stretching the PTFE layer while the layer is wet with stretching agent. For some embodiments, the PTFE layer may be saturated with stretching agent while being stretched. For some embodiments, the PTFE layer may be stretched by a ratio of about 2:1 to about 20:1. For some embodiments, the wet stretching of the PTFE layer is carried out in a direction transverse to the machine direction of expansion. For some embodiments, the wet stretching of the PTFE layer is carried out at a temperature of about 80° F. to about 130° F. For some embodiments, the PTFE layer provided is made by extruding a compounded PTFE resin through an extruder to form a PTFE ribbon extrudate. Such a PTFE material may have substantially low porosity, low permeability, no discernable node and fibril structure and a thickness of about 0.00005 inch to about 0.005 inch. Some such PTFE materials may also have a closed cell microstructure with a plurality of interconnected high density regions having no discernable node and fibril structure between the high density regions. Some such PTFE materials may have low or no fluid permeability.

The transverse dimension or diameter of the main fluid flow lumen of some main graft embodiments 112 in a radially expanded state may be from about 12.0 mm to about 32.0 mm. The transverse dimension or diameter of the first and second branched leg fluid flow lumens 146, 148 may be from about 5 mm to about 20 mm for some embodiments. For some embodiments, the length of the legs 118 and 120 and may be from about 2 cm to about 6 cm. The transverse dimension of some embodiments of the graft extensions 142 and 144 when in a radially expanded state may be from about 5 mm to about 26 mm. The axial length of some embodiments of the graft extensions 142 and 144 may be from about 2 cm to about 15 cm, specifically, about 5 cm to about 10 cm. Some embodiments of the first and second extension grafts 142 and 144 may have outer transverse dimensions or diameters of between about 10 mm to about 30 mm, more specifically, between about 15 mm and 25 mm when in an expanded state.

The main graft 112 and graft portions of the first and second graft extensions 142 and 144 may be made at least partially from polytetrafluoroethylene (PTFE) which may include expanded polytetrafluoroethylene (ePTFE). In particular, main graft 112 and graft extensions 142 and 144 may include any number of layers of PTFE and/or ePTFE, including from about 2 to about 15 layers, having an uncompressed layered thickness of about 0.003 inch to about 0.015 inch for the supple graft material or materials alone without supporting or ancillary structures such as high strength stents, connector rings or the like. Such graft body sections may also include any alternative high strength, supple biocompatible materials, such as DACRON, suitable for graft applications. Descriptions of various constructions of graft body sections as well as other components of graft assembly 110 that may be used in any suitable combination for any of the embodiments discussed herein may be found in U.S. Pat. No. 7,125,464 to Chobotov, et al., entitled "Method and Apparatus for Manufacturing an Endovascular Graft Section"; U.S. Pat. No. 7,090,693 to Chobotov et al., entitled "Endovascular Graft Joint and Method of Manufacture"; U.S. Pat. No. 7,147,661, entitled "Method and Apparatus for Shape Forming Endovascular Graft Material", to Chobotov et al.; U.S. Pat. No. 7,147,660 to by Chobotov et al., entitled "Advanced Endovascular Graft"; U.S. Patent Application Publication No. US 2006/0233990 to Humphrey et al. entitled "PTFE Layers and Methods of Manufacturing"; and U.S. Patent Application Publication No. 2006/0233991 to Humphrey et al., entitled "PTFE Layers and Methods of Manufacturing", the entirety of each of which is incorporated herein by reference.

It may be useful for some embodiments of the main graft 112 to have a nominal axial length which is configured to allow the use of the main graft 112 in a wide variety of vascular morphologies with supplementation by one or more graft extensions 142 and 144. A modular graft embodiment 110 is normally chosen in order to have a proper fit to the patient's vasculature. For some graft indications, it is necessary to produce a large number of size variations of the graft system, or graft assembly 110 components, in order to accommodate the size and configuration variations of each patient's vasculature in order to achieve an acceptable fit of the graft assembly 110 within the patient's vasculature. This can be very costly and time consuming for the manufacturer of the endovascular graft assembly 110 and the hospitals which must maintain a comprehensive inventory of the devices. In addition, this may require an inconvenient amount of shelf space in the hospital operating room or catheter lab. For some embodiments, main graft member 112 may have an axial length that is selected to allow anchoring of the proximal anchor member 122 adjacent the renal arteries extending from a patient's aorta with the legs of the bifurcated portion remaining clear of the iliac arteries in a large cross section of patients having diverse physical size and vascular configurations. In this way, the need for customizing a graft assembly 110 for a particular patient or group of patients can be avoided.

For some embodiments, the axial length of the main graft member 112, and particularly the axial distance or separation between the proximal anchor member 122 and distal end of the first and second branched legs 118 and 120 may be selected to extend across an abdominal aortic aneurysm without extending into the iliac arteries of a selected patient. A selected patient may be a member of a group of patients who has the longest axial separation between the sealing point in the aorta just distal to the renal arteries and a distal most viable anchor and sealing point in the iliac arteries. In some embodiments for a particular patient group, the proximal end of the main graft member 112 is axially separated from the distal ends of the first and second branched legs 118 and 120 by a length of about 5 cm to about 10 cm, more specifically, about 6 cm to about 8 cm.

For some embodiments of sizing a main graft member embodiment 112, the separation of the proximal anchor member 122 and distal end of deployed graft extensions 142 and 144 is selected such that the separation is just long enough to span the separation between the renal arteries and the proximal most anchor and sealing point in the iliac artery or arteries of a patient. This distance may be determined from the patient, in a selected group of patients, which has the longest such separation in the selected group of patients. In addition, for these embodiments, this separation must be shorter than the separation between the renal arteries and hypogastric artery or arteries. The distance may be determined from the patient, in the selected group of patients, that has the shortest such separation in the selected group of patients. In this way, it may be possible to treat all members of a selected group of patients with a main graft member 112 embodiment or embodiments which have a common main graft body length. Such embodiments may be anchored to the patient's aorta distal of the patient's renal arteries and anchored distally in the patient's iliac artery or arteries, without blocking either the renal arteries or hypogastric artery or arteries. Such a modular graft system embodiment 110 may have an overall length including the main graft member 112 and deployed graft extensions 142, 144 of about 10 cm to about 22 cm, specifically, about 11 cm to about 20 cm.

The careful sizing and configuring of the main graft 112 allows the use of a single main graft 112 embodiment or design to be adaptable to a wide range of patients when supplemented by one or more graft extensions 142, 144. More specifically, a main graft 112 having an axial length of about 5 cm to about 8 cm may be properly deployed in a large percentage of potential patients. Once deployed, the fluid flow lumens 146, 148 of the first and second graft extensions 142, 144 can then be sealed to the patient's iliac arteries 170 with the deployment of graft extensions 142, 144. Although the graft assembly 110 includes the option of using attachment elements to secure the graft extensions 142, 144 to the first and second branched legs 118, 120, this may not be necessary in most cases and an adequate seal and mechanical fixation of a graft extensions 142, 144 may be achieved with the use of a standard expandable member on the graft extensions 142, 144 instead of an attachment element.

Some embodiments of a method of treating a patient include providing a delivery catheter containing a radially constrained bifurcated main graft member 110. For some method embodiments of treating the vasculature of a patient, a modular graft assembly, such as the modular graft assembly embodiments 110 discussed above, may be used. For endovascular methods, access to a patient's vasculature may be achieved by performing an arteriotomy or cut down to the patient's femoral artery or by other common techniques, such as the percutaneous Seldinger technique. For such techniques, a delivery sheath (not shown) may be placed in communication with the interior of the patient's vessel such as the femoral artery with the use of a dilator and guidewire assembly. Once the delivery sheath is positioned, access to the patient's vasculature may be achieved through the delivery sheath which may optionally be sealed by a hemostasis valve or other suitable mechanism. For some procedures, it may be necessary to obtain access via a delivery sheath or other suitable means to both femoral arteries of a patient with the delivery sheaths directed upstream towards the patient's vessel 164 (such as the aorta). In some applications a delivery sheath may not be needed and the delivery catheter may be directly inserted into the patient's access vessel by either arteriotomy or percutaneous puncture.

Figure 8:
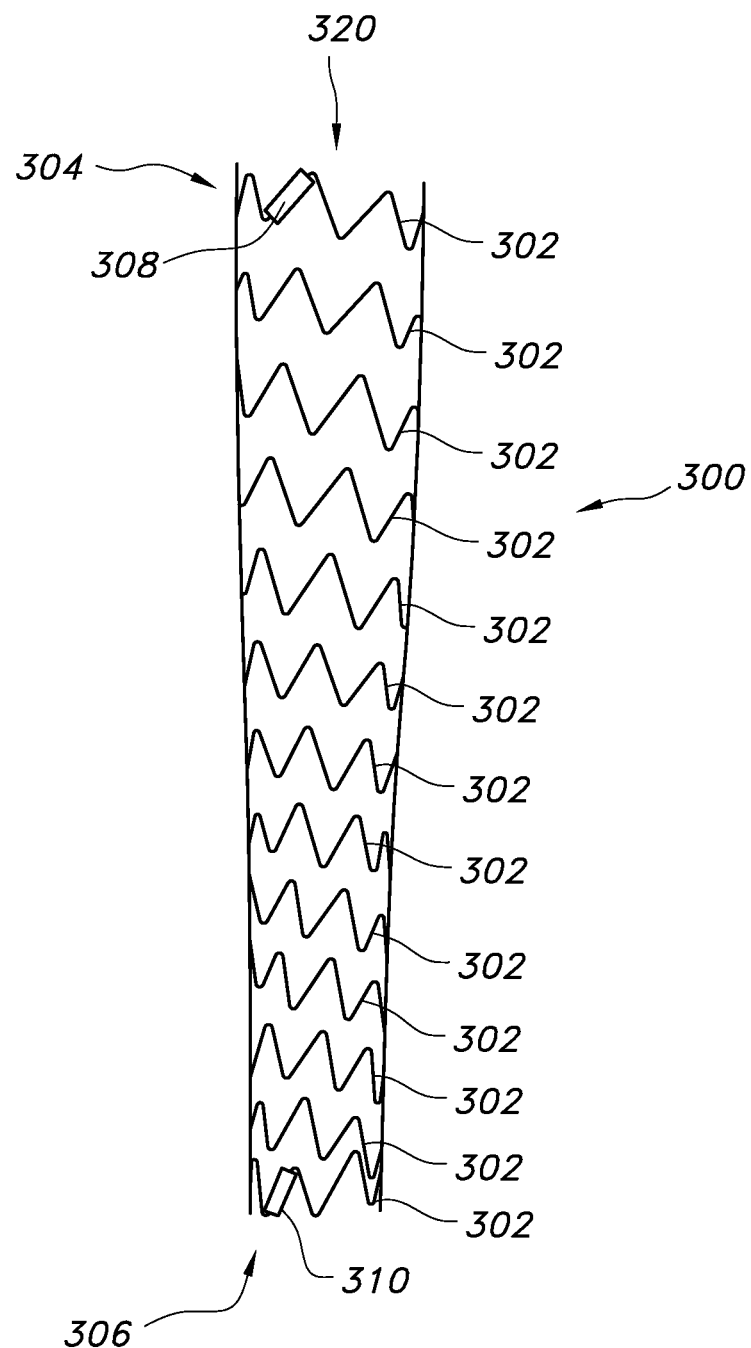
FIG. 8 depicts one embodiment of a stent structure useful in the present invention.

Once the proximal anchor member 122 has been secured to the inside surface 166 of the patient's vessel 164, the proximal inflatable channels 128 (and in particular, the inflatable channel acting as a cuff 128') may then be filled through an inflation port in either the first inflation fill channel 134 or the second inflatable fill channel 136 with inflation material injected through an inflation tube. Such inflation may serve to seal an outside surface of the inflatable cuff 128' to the inside surface 166 of the vessel 164. The remaining network of inflatable channels 128, 130, 132 are also filled with pressurized inflation material at the same time which provides a more rigid frame like structure to the graft 112 as shown in FIG. 8. In addition, the first and second longitudinal inflation channels 138, 140 are filled with pressurized inflation material, giving even more strength and rigidity. For some embodiments, the inflation material may be a curable or hardenable material that may cured or hardened once the network of inflatable channels are filled to a desired level of material or pressure within the network. Some embodiments may also employ radiopaque inflation material to facilitate monitoring of the fill process and subsequent engagement of graft extensions. The material may be cured by any of the suitable methods discussed herein including time lapse, heat application, application of electromagnetic energy, ultrasonic energy application, chemical adding or mixing or the like.

The network of inflatable channels 128, 130, 132, and the longitudinal inflation channels 138, 140, may be partially or fully inflated by injection of a suitable inflation material into the main fill port to provide rigidity to the assembly 110. Although it is desirable to partially or fully inflate the network of inflatable channels 128, 130, 132 of the main graft 112 at an early stage of the deployment process, such inflation step optionally may be accomplished at a later stage if necessary.

For some embodiments, up to the time that the network of inflatable channels 128, 130, 132, including the longitudinal inflation channels 138, 140, have been filled with inflation material which has been cured or hardened, an elongate tether may be used to axially restrain the graft 112 and prevent axial separation of the graft 112 from the delivery catheter. A tether loops through the first and second lumens of the first and second branched legs 118, 120 of the graft member 112 and is secured to a handle on a proximal adapter (not shown) of the delivery catheter. The tether is configured to have a length that is short enough to mechanically restrain distal axial movement of the main graft member 112 relative to the delivery catheter so as to prevent decoupling of an inflation tube from the inflatable fill channel 134, 136 of the main graft member 112. Once the inflation material has been fully injected into the network of inflatable channels 128, 130, 132, including the longitudinal inflation channels 138, 140 and cured or hardened, the tether may be released and removed to allow distal retraction of the delivery catheter.

The following embodiments or aspects of the invention may be combined in any fashion and combination and be within the scope of the present invention, as follows:

Embodiment 1. An endovascular stent-graft comprising:
  a tubular stent wall having opposed first and second ends;
  an undulating wire having opposed first and second ends and being helically wound into a plurality of approximate circumferential windings to define said stent wall;
  said undulating wire having a plurality undulations defined by peaks and valleys;
  peaks of adjacent approximate circumferential windings being separated by a distance with said distance between adjacent peaks at said first end being different from said distance between adjacent peaks at said second end;
  said first wire end secured to a first undulation at said first end;
  said second wire end secured to a second undulation at said second end;
  a graft liner comprising first plurality of layers of porous PTFE having no discernable node and fibril structure; and
  a graft covering comprising a second plurality of layers of porous PTFE having no discernable node and fibril structure;
  wherein said tubular stent wall is securably disposed between said graft covering and said graft lining.

Embodiment 2. The endovascular stent-graft of embodiment 1, wherein said peaks of one circumferential winding are substantially aligned with said peaks of an adjacent circumferential winding.

Embodiment 3. The endovascular stent-graft of embodiment 1, wherein said peaks of one circumferential winding are substantially aligned with said valleys of an adjacent circumferential winding.

Embodiment 4. The endovascular stent-graft of embodiment 1, wherein said endovascular stent-graft has a longitudinal axis and a radial axis perpendicular to said longitudinal axis; and
  wherein said undulating wire is helically wound at an acute winding angle of about 3 degrees to about 15 degrees with respect to said radial axis.

Embodiment 5. The endovascular stent-graft of embodiment 4, wherein said acute winding angle at a portion of said stent wall proximal to said first end of said stent wall is different from said acute winding angle at a portion of said stent wall proximal to said second end of said stent wall.

Embodiment 6. The endovascular stent-graft of embodiment 4, a first winding at said first end is perpendicular to said longitudinal axis and wherein a terminal winding at said second end is perpendicular to said longitudinal axis.

Embodiment 7. The endovascular stent-graft of embodiment 1, wherein an adjacent peak and an adjacent valley of said undulating wire has a peak height from an apex of said adjacent peak to a base of said adjacent valley; and wherein said peak height at a portion of said stent wall proximal to said first end of said stent wall is different from said peak height at a portion of said stent wall proximal to said second end of said stent wall.

Embodiment 8. The endovascular stent-graft of embodiment 1, wherein, except for said first and said second wire ends being secured to said first and second undulations, respectively, adjacent approximate circumferential windings are free of interconnecting struts and welds.

Embodiment 9. The endovascular stent-graft of embodiment 1, wherein said graft liner and said graft covering is crimped between said peaks of adjacent approximate circumferential windings to provide crimped graft portions.

Embodiment 10. The endovascular stent-graft of embodiment 10, wherein said crimped graft portions are approximate circumferential crimped portions.

Embodiment 11. An endovascular stent-graft comprising:
  a graft liner comprising first plurality of layers of porous PTFE having no discernable node and fibril structure;
  a graft covering comprising a second plurality of layers of porous PTFE having no discernable node and fibril structure; and
  a tubular stent securably disposed between said graft liner and said graft cover; said stent comprising an undulating wire having opposed first and second ends and being helically wound into a plurality of approximate circumferential windings to define a stent wall; said undulating wire having a plurality undulations defined by peaks and valleys with peaks of adjacent approximate circumferential windings being separated by a distance;
  wherein said graft liner and said graft covering is crimped between said peaks of adjacent approximate circumferential windings to provide crimped graft portions.

Embodiment 12. The endovascular stent-graft of embodiment 11, wherein said crimped graft portions are approximate circumferential crimped portions.

Embodiment 13. A method of making a crimped stent graft, comprising the steps of:
  a. providing a tubular stent having an inner surface and an outer surface, said stent comprising an undulating wire having opposed first and second ends and being helically wound into a plurality of approximate circumferential windings to define a stent wall; said undulating wire having a plurality undulations defined by peaks and valleys with peaks of adjacent approximate circumferential windings being separated by a distance;
  b. axially stretching said tubular stent;
  c. disposing a graft liner on said inner surface of said axially stretched tubular stent, said graft liner comprising first plurality of layers of porous PTFE having no discernable node and fibril structure;

d. disposing a graft covering on said outer surface of said axially stretched tubular stent, said graft covering comprising a second plurality of layers of porous PTFE having no discernable node and fibril structure; and e. allowing said axially stretched tubular stent to relax, forming crimps in said graft liner and said graft covering.

Embodiment 14. A method of making a crimped stent graft, comprising the steps of:

a. providing a tubular stent having an inner surface and an outer surface, said stent comprising an undulating wire having opposed first and second ends and being helically wound into a plurality of approximate circumferential windings to define a stent wall; said undulating wire having a plurality undulations defined by peaks and valleys with peaks of adjacent approximate circumferential windings being separated by a distance;

b. disposing a graft liner on said inner surface of said tubular stent, said graft liner comprising first plurality of layers of porous PTFE having no discernable node and fibril structure;

c. disposing a graft covering on said outer surface of said tubular stent, said graft covering comprising a second plurality of layers of porous PTFE having no discernable node and fibril structure;

d. placing said tubular stent, graft liner and graft cover on a shaped mandrel, said shaped mandrel including at least one crimp shape on its outer surface; and e. heating and sintering said tubular stent, graft liner and graft cover so as to form a crimped stent graft comprising at least one crimp conforming to the crimp shape of said shaped mandrel.

Embodiment 15. An inflatable endovascular graft comprising:

a tubular graft having opposed first and second open ends and having a first graft portion proximal to said first end and a second graft portion proximal to said second end;

at least one circumferential inflatable channel disposed at said first graft portion;

at least two circumferential inflatable channels disposed at said second graft portion;

a longitudinal inflatable fill channel disposed between said first end and said second end of said graft and in fluid communication with said at least one circumferential inflatable channel disposed at said first graft portion and said at least two circumferential inflatable channels disposed at said second graft portion; and a first longitudinal inflatable channel disposed along said second graft portion and traversing said at least two circumferential inflatable channels disposed at said second graft portion, wherein said first longitudinal inflatable channel is in fluid communication with said at least two circumferential inflatable channels disposed at said second graft portion.

Embodiment 16. The inflatable endovascular graft of embodiment 15, wherein said first longitudinal inflatable channel comprises a plurality of channels.

Embodiment 17. The inflatable endovascular graft of embodiment 15, wherein said second end is bifurcated.

Embodiment 18. The inflatable endovascular graft of embodiment 15, wherein second graft portion includes a circumference and at least one of said at least two circumferential inflatable channels completely traverses said circumference of said second graft portion.

Embodiment 19. The inflatable endovascular graft of embodiment 15, wherein second graft portion includes a circumference and at least one of said at least two circumferential inflatable channels partially traverses said circumference of said second graft portion.

Embodiment 20. A bifurcated inflatable endovascular graft comprising:

a tubular graft having a first end and an opposed second end, said second end being a bifurcated end having a first branch and a second branch, said first end having a first graft portion proximal to said first end, said first branch having a first branch portion proximal to said second end, said second branch having a second branch portion proximal to said second end;

at least one circumferential inflatable channel disposed at said first graft portion;

at least two circumferential inflatable channels disposed at said first branch portion;

at least two circumferential inflatable channels disposed at said second branch portion;

a first longitudinal inflatable fill channel disposed between said first end and said end of said first branch portion, said first longitudinal inflatable fill channel being in fluid communication with said at least one circumferential inflatable channel disposed at said first graft portion and said at least two circumferential inflatable channels disposed at said first branch portion;

a second longitudinal inflatable fill channel disposed between said first end and said end of said second branch portion, said second longitudinal inflatable fill channel being in fluid communication with said at least one circumferential inflatable channel disposed at said first graft portion and said at least two circumferential inflatable channels disposed at said second branch portion; and a first longitudinal inflatable channel disposed along said first branch portion and traversing said at least two circumferential inflatable channels disposed at said first branch portion, wherein said first longitudinal inflatable channel is in fluid communication with said at least two circumferential inflatable channels disposed at said first branch portion.

Embodiment 21. The bifurcated inflatable endovascular graft of embodiment 20, further comprising a second longitudinal inflatable channel disposed along said second branch portion and traversing said at least two circumferential inflatable channels disposed at said second branch portion, wherein said second longitudinal inflatable channel is in fluid communication with said at least two circumferential inflatable channels disposed at said second branch portion.

Embodiment 22. The bifurcated inflatable endovascular graft of embodiment 20, wherein said first branch portion includes a circumference and at least one of said at least two circumferential inflatable channels at said first branch portion completely traverses said circumference of said first branch portion.

Embodiment 23. The bifurcated inflatable endovascular graft of embodiment 22, wherein one of said at least two circumferential inflatable channels at said first branch is disposed at a location furthest from said first end, the one of at least two circumferential inflatable channels at said first branch disposed at a location furthest from said first end completely traversing said circumference of said first branch portion.

Embodiment 24. The bifurcated inflatable endovascular graft of embodiment 20, wherein first branch portion includes a circumference and at least one of said at least two circumferential inflatable channels at said first branch portion partially traverses said circumference of said first branch portion.

Embodiment 25. The bifurcated inflatable endovascular graft of embodiment 20, wherein second branch portion includes a circumference and at least one of said at least two circumferential inflatable channels at said second branch portion completely traverses said circumference of said second branch portion.

Embodiment 26. The bifurcated inflatable endovascular graft of embodiment 25, wherein one of said at least two circumferential inflatable channels at said second branch is disposed at a location furthest from said first end, the one of at least two circumferential inflatable channels at said second branch disposed at a location furthest from said first end completely traversing said circumference of said second branch portion.

Embodiment 27. The bifurcated inflatable endovascular graft of embodiment 20, wherein second branch portion includes a circumference and at least one of said at least two circumferential inflatable channels at said second branch portion partially traverses said circumference of said second branch portion.

Embodiment 28. A modular endovascular graft comprising:
a tubular graft having a first end and an opposed second end, said second end being a bifurcated end having a first branch and a second branch, said first end having a first graft portion proximal to said first end, said first branch having a first branch portion proximal to said second end, said second branch having a second branch portion proximal to said second end;
at least one circumferential inflatable channel disposed at said first graft portion;
at least two circumferential inflatable channels disposed at said first branch portion;
at least two circumferential inflatable channels disposed at said second branch portion;
a first longitudinal inflatable fill channel disposed between said first end and said end of said first branch portion and in fluid communication with said at least one circumferential inflatable channel disposed at said first graft portion and said at least two circumferential inflatable channels disposed at said first branch portion;
a second longitudinal inflatable fill channel disposed between said first end and said end of said second branch portion and in fluid communication with said at least one circumferential inflatable channel disposed at said first graft portion and said at least two circumferential inflatable channels disposed at said second branch portion;
a first longitudinal inflatable channel dispose along said first branch portion and traversing said at least two circumferential inflatable channels disposed at said first branch portion, wherein said first longitudinal inflatable channel is in fluid communication with said at least two circumferential inflatable channels disposed at said first branch portion;
a second longitudinal inflatable channel dispose along said second branch portion and traversing said at least two circumferential inflatable channels disposed at said second branch portion, wherein said second longitudinal inflatable channel is in fluid communication with said at least two circumferential inflatable channels disposed at said second branch portion.
a first stent-graft securable to said first branch portion; and
a second stent-graft securable to said second branch portion.

Embodiment 29. The modular graft of embodiment 28, wherein at least one of said first stent-graft and said second stent-graft comprises:
a tubular stent wall having opposed first and second ends;
an undulating wire having opposed first and second ends and being helically wound into a plurality of approximate circumferential windings to define said stent wall;
said undulating wire having a plurality undulations defined by peaks and valleys;
wherein peaks of adjacent approximate circumferential windings are separated by a distance, said distance between adjacent peaks at said first end being different from said distance between adjacent peaks at said second end.

Embodiment 30. The modular graft of embodiment 29, wherein said first wire end is secured to a first undulation at said first end and said second wire end is secured to a second undulation at said second end.

Embodiment 31. The modular graft of embodiment 29, further comprising:
a graft liner comprising first plurality of layers of porous PTFE having no discernable node and fibril structure; and
a graft covering comprising a second plurality of layers of porous PTFE having no discernable node and fibril structure;
wherein said tubular stent wall is securably disposed between said graft covering and said graft lining.

Embodiment 32. The modular graft of embodiment 31, wherein said graft liner of said at least one of said first stent-graft and said second stent-graft and said graft covering of said at least one of said first stent-graft and said second stent-graft is crimped between said peaks of adjacent approximate circumferential windings to provide crimped graft portions.

Embodiment 33. The modular graft of embodiment 32, wherein said crimped graft portions are approximate circumferential crimped portions.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed is:
1. An endovascular stent-graft comprising:
a tubular stent wall having opposed first and second ends;
an undulating wire having opposed first and second ends and being helically wound into a plurality of approximate circumferential windings to define said stent wall;
said undulating wire having a plurality undulations defined by peaks and valleys;
peaks of adjacently juxtaposed circumferential windings being separated by a distance (X) with said distance at said first end being different from said distance at said second end;
said first wire end secured to a first undulation at said first end;
said second wire end secured to a second undulation at said second end;
a graft liner comprising first plurality of layers of porous PTFE having no discernable node and fibril structure; and a graft covering comprising a second plurality of layers of porous PTFE having no discernable node and fibril structure;

wherein said tubular stent wall is securably disposed between said graft covering and said graft lining;

wherein said endovascular stent-graft has a longitudinal axis and a radial axis perpendicular to said longitudinal axis; and wherein said undulating wire is helically wound at an acute winding angle of 3 degrees to 15 degrees with respect to said radial axis;

wherein said acute winding angle at a portion of said stent wall proximal to said first end of said stent wall is different from said acute winding angle at a portion of said stent wall proximal to said second end of said stent wall;

wherein said peaks and valleys of said undulating wire have a peak height (Y) from an apex of one peak to a base of an adjacently juxtaposed valley;

wherein a ratio of said distance between peaks of adjacently juxtaposed circumferential windings to the peak height (X/Y) is from −0.1 to 0.3 at said second end; and wherein the graft liner and the graft covering has a combined thickness from 0.003 inches to 0.015 inches.

2. The endovascular stent-graft of claim 1, wherein said peaks of one circumferential winding are substantially aligned with said peaks of an adjacently juxtaposed circumferential winding.

3. The endovascular stent-graft of claim 1, wherein said peaks of one circumferential winding are substantially aligned with said valleys of an adjacently juxtaposed circumferential winding.

4. The endovascular stent-graft of claim 1, wherein said acute winding angle at a portion of said stent wall proximal to said first end of said stent wall is different from said acute winding angle at a portion of said stent wall proximal to said second end of said stent wall.

5. The endovascular stent-graft of claim 1, wherein a first winding at said first end is perpendicular to said longitudinal axis and wherein a terminal winding at said second end is perpendicular to said longitudinal axis.

6. The endovascular stent-graft of claim 1, wherein, except for said first and said second wire ends being secured to said first and second undulations, respectively, adjacently juxtaposed circumferential windings are free of interconnecting struts and welds.

7. The endovascular stent-graft of claim 1, wherein said graft liner and said graft covering is crimped between said peaks of adjacently juxtaposed circumferential windings to provide crimped graft portions.

8. The endovascular stent-graft of claim 7, wherein said crimped graft portions are circumferential crimped portions.

9. The endovascular stent-graft of claim 1, wherein said endovascular stent-graft wall has a diameter and wherein the peak height (Y) is from one fifth to one half of said diameter.

* * * * *